US012778765B2

(12) United States Patent
Cain et al.

(10) Patent No.: US 12,778,765 B2
(45) Date of Patent: Nov. 3, 2026

(54) INTERBODY LATTICE STRUCTURE

(71) Applicant: MiRus LLC, Marietta, GA (US)

(72) Inventors: David Brett Cain, Marietta, GA (US); Noah Roth, Marietta, GA (US); Jay Yadav, Marietta, GA (US)

(73) Assignee: MiRus LLC, Marietta, GA (US)

(*) Notice: Subject to any disclaimer, the term of this patent is extended or adjusted under 35 U.S.C. 154(b) by 123 days.

(21) Appl. No.: 18/507,642

(22) Filed: Nov. 13, 2023

(65) Prior Publication Data

US 2024/0074870 A1 Mar. 7, 2024

Related U.S. Application Data

(63) Continuation of application No. 17/529,760, filed on Nov. 18, 2021, now Pat. No. 11,911,285, which is a continuation of application No. 16/893,857, filed on Jun. 5, 2020, now Pat. No. 11,273,048, which is a continuation of application No. 29/706,986, filed on Sep. 25, 2019, now Pat. No. Des. 898,197.

(60) Provisional application No. 62/981,895, filed on Feb. 26, 2020.

(51) Int. Cl.
*A61F 2/44* (2006.01)
*A61F 2/30* (2006.01)

(52) U.S. Cl.
CPC ........ *A61F 2/4425* (2013.01); *A61F 2/30767* (2013.01); *A61F 2/3094* (2013.01); *A61F 2/4465* (2013.01); *A61F 2002/3092* (2013.01); *A61F 2002/3093* (2013.01); *A61F 2002/30985* (2013.01); *A61F 2002/443* (2013.01)

(58) Field of Classification Search
CPC ......................... A61F 2/44–447; A61F 2/4611
See application file for complete search history.

(56) References Cited

U.S. PATENT DOCUMENTS

| | | | |
|---|---|---|---|
| 3,867,728 A | 2/1975 | Stubstad et al. | |
| 4,457,984 A | 7/1984 | Otani et al. | |
| 4,955,908 A * | 9/1990 | Frey | A61F 2/442 606/907 |
| 5,496,372 A | 3/1996 | Hamamoto et al. | |
| 5,545,229 A | 8/1996 | Parsons et al. | |
| 5,609,635 A | 3/1997 | Michelson | |
| 7,001,551 B2 | 2/2006 | Meredith | |
| D652,821 S | 1/2012 | Lee et al. | |
| 9,295,562 B2 | 3/2016 | Lechmann et al. | |
| 9,345,817 B2 | 5/2016 | Papengelou et al. | |
| D773,047 S | 11/2016 | Goncalves et al. | |
| 9,636,226 B2 | 5/2017 | Hunt | |
| 9,662,157 B2 | 5/2017 | Schneider et al. | |

(Continued)

OTHER PUBLICATIONS

International Search Report and Written Opinion for International Application No. PCT/US2020/036277 dated Aug. 19, 2020.

*Primary Examiner* — Eduardo C Robert
*Assistant Examiner* — Steven J Cotroneo
(74) *Attorney, Agent, or Firm* — UB Greensfelder LLP; Brian E. Turung

(57) ABSTRACT

An orthopedic implant which generally includes a frame structure and a porous structure. Both the frame and porous structure at least partially define at least six surfaces which make a three-dimensional profile of the implant. The porous structure is positioned at least partially within the three-dimensional profile.

12 Claims, 7 Drawing Sheets

(56) References Cited

U.S. PATENT DOCUMENTS

| | | | | |
|---|---|---|---|---|
| 9,681,966 | B2 | 6/2017 | Knapp et al. | |
| 9,700,431 | B2 | 7/2017 | Nebosky et al. | |
| 9,724,203 | B2 * | 8/2017 | Nebosky | A61F 2/442 |
| D809,661 | S | 2/2018 | Mueller | |
| D815,281 | S | 4/2018 | Chang et al. | |
| 10,271,958 | B2 | 4/2019 | Schaufler et al. | |
| D870,288 | S | 12/2019 | Dang | |
| 10,512,545 | B2 | 12/2019 | Arnone | |
| 10,517,739 | B2 * | 12/2019 | Ryan | A61F 2/4455 |
| 10,709,570 | B2 * | 7/2020 | Stauffer | A61F 2/4455 |
| 11,273,048 | B2 | 3/2022 | Cain et al. | |
| 11,911,285 | B2 * | 2/2024 | Cain | A61F 2/30767 |
| 2009/0048675 | A1 | 2/2009 | Bhatnagar et al. | |
| 2012/0197413 | A1 | 8/2012 | Kyomoto et al. | |
| 2012/0239152 | A1 | 9/2012 | Ulrich, Jr. et al. | |
| 2012/0303128 | A1 | 11/2012 | Ulrich et al. | |
| 2012/0321878 | A1 * | 12/2012 | Landon | A61L 27/56 264/497 |
| 2016/0324656 | A1 | 11/2016 | Morris et al. | |
| 2017/0156880 | A1 * | 6/2017 | Halverson | A61F 2/4455 |
| 2018/0243097 | A1 * | 8/2018 | Jones | B33Y 50/00 |
| 2018/0296363 | A1 | 10/2018 | Berry | |
| 2019/0083270 | A1 * | 3/2019 | Milz | A61F 2/4455 |
| 2019/0133783 | A1 * | 5/2019 | Unger | A61F 2/44 |

* cited by examiner

INTERBODY LATTICE STRUCTURE

The present disclosure is a continuation of U.S. application Ser. No. 17/529,760 filed Nov. 18, 2021, which in turn is a continuation of U.S. application Ser. No. 16/893,857 filed Jun. 5, 2020 (now U.S. Pat. No. 11,273,048), which in turn claims priority on U.S. Provisional Application Ser. No. 62/981,895 filed Feb. 26, 2020, all of which are incorporated herein by reference.

The present disclosure is a continuation of U.S. application Ser. No. 17/529,760 filed Nov. 18, 2021, which in turn is a continuation of U.S. application Ser. No. 16/893,857 filed Jun. 5, 2020 (now U.S. Pat. No. 11,273,048), which in turn claims priority on U.S. application Ser. No. 29/706,986 filed Sep. 25, 2019, all of which are incorporated herein by reference.

The present disclosure generally relates to implant devices and systems for insertion between at least two adjacent vertebrae, but also can include the placement of an implant between one or more other types of bones to provide fixation and/or integration of the implant into the bone contacting the implant. In particular, the present disclosure sets forth an orthopedic implant which generally includes a frame structure and a porous lattice structure. Both the frame and porous structure at least partially define surfaces which make a three-dimensional profile of the implant, and the porous structure is positioned at least partially within the three-dimensional profile.

BACKGROUND OF THE DISCLOSURE

The spine is the axis of the skeleton upon which all the body parts "hang". In humans, the normal spine has seven cervical, twelve thoracic, and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated herniated discs, the disc is removed along with all or part of at least one neighboring vertebrae and is replaced by an implant that promotes fusion of the remaining bony anatomy.

However, the success or failure of bony fusion may depend upon several factors. For instance, the spacer or implant or cage used to fill a space or change the orientation and distance between two naturally occurring bony structures must be sufficiently strong to support the bones under a wide range of loading conditions. The spacer should also be configured so that it is likely to remain in place once it has been positioned by a surgeon. Additionally, the material used for the spacer should be biocompatible material and should have a configuration that promotes bony ingrowth.

BRIEF DESCRIPTION

To meet this and other needs, the orthopedic implant device may generally include a frame structure and a porous structure. Both the frame and porous structure at least partially define surfaces which make a three-dimensional profile of the implant. The porous structure is positioned at least partially within the three-dimensional profile.

In one non-limiting embodiment of the disclosure, there is provided an interbody implant device that enables bone to grow into and/or through a portion thereof, making it part of the fusion mass.

In another and/or alternative non-limiting embodiment of the disclosure, there is provided an interbody implant device that can be formed by additive manufacturing, or 3D printing.

In another and/or alternative non-limiting embodiment of the disclosure, there is provided an interbody implant device that may be manufactured utilizing a combination of additive manufacturing processes and other manufacturing processes, for example, laser etching.

In another and/or alternative non-limiting embodiment of the disclosure, there is provided an interbody implant device that may be further processed during and/or after manufacture utilizing various techniques, for example, abrasion, machining, polishing, or chemical treatment.

In another and/or alternative non-limiting embodiment of the disclosure, there is provided an interbody implant device that is manufactured from various materials, such as biocompatible materials, including metals, polymers, ceramics or combinations thereof. Exemplary materials include metal materials (e.g., titanium, titanium alloys, cobalt-chrome alloys, stainless steel, molybdenum alloys, rhenium alloys, molybdenum-rhenium alloys, tungsten alloys, etc.) and polymers (e.g., PEEK, etc.).

In another and/or alternative non-limiting embodiment of the disclosure, there is provided an interbody implant device that is specially adapted for use between bony structures and generally includes at least six unique surfaces which define a body or three-dimensional ("3D") profile.

In another and/or alternative non-limiting embodiment of the disclosure, there is provided an interbody implant device wherein the top and bottom surfaces may generally be oriented along converging planes, diverging planes, and/or parallel planes.

In another and/or alternative non-limiting embodiment of the disclosure, there is provided an interbody implant device that optionally includes an aperture formed in the rear plate that provides a screw opening configured to provide a rigid connection with a tool or instrument used for inserting the interbody implant device.

In another and/or alternative non-limiting embodiment of the disclosure, there is provided an interbody implant device that includes plate elements and rim elements which are all generally connected to the porous structure.

In another and/or alternative non-limiting embodiment of the disclosure, there is provided an interbody implant device that includes outer top and bottom rims that are spaced apart from one another and are each configured to provide at least one point of connection with the plate members.

In another and/or alternative non-limiting embodiment of the disclosure, there is provided an interbody implant device that includes a rear wall that covers about 5-100% of the rear surface of the interbody implant device.

In another and/or alternative non-limiting embodiment of the disclosure, there is provided an interbody implant device that includes a top front plate that is connected to the outer top rim and the bottom front plate is connected to the outer bottom rim on the front wall, and the top and bottom front plates are also spaced from one another to form a front plate gap on the front wall.

In another and/or alternative non-limiting embodiment of the disclosure, there is provided an interbody implant device that includes a front plate gap that advantageously allows for the load applied to the porous structure, thereby reducing the stiffness of the body profile of the interbody implant device.

In another and/or alternative non-limiting embodiment of the disclosure, there is provided an interbody implant device that includes a top front plate and bottom front plate that covers 15-98% (and all values and ranges therebetween) of the front surface of the interbody implant device.

In another and/or alternative non-limiting embodiment of the disclosure, there is provided an interbody implant device that includes top and/or bottom front plates that can optionally form 0-60% (and all values and ranges therebetween) of one or both sides of the interbody implant device.

In another and/or alternative non-limiting embodiment of the disclosure, there is provided an interbody implant device that includes an outer top rim and an outer bottom rim that are optionally formed of smooth surfaces so as to reduce or eliminate any sharp outer peripheral surfaces on the outer top rim and/or the outer bottom rim.

In another and/or alternative non-limiting embodiment of the disclosure, there is provided an interbody implant device wherein no portion of the frame structure provides support to the sidewalls.

In another and/or alternative non-limiting embodiment of the disclosure, there is provided an interbody implant device wherein only the outer top rim and/or the outer bottom rim forms a portion of the one or both side surfaces of the interbody implant device.

In another and/or alternative non-limiting embodiment of the disclosure, there is provided an interbody implant device that includes one or more surface serrations or teeth formed on the outer top and/or bottom rim to help prevent the interbody implant device from backing out after the device has been inserted.

In another and/or alternative non-limiting embodiment of the disclosure, there is provided an interbody implant device that optionally includes a central opening defined within an inner perimeter of the body profile, wherein the central opening is generally configured to receive one or more materials including, but not limited to, bone growth-promoting materials, drugs, and cartilage, for example.

In another and/or alternative non-limiting embodiment of the disclosure, there is provided an interbody implant device that optionally includes an undercut formed in the central opening on the inner top and/or bottom rim that is at least partial void of porous material, which undercut increases the amount of material which can be packed into the central opening.

In another and/or alternative non-limiting embodiment of the disclosure, there is provided an interbody implant device that has a Ra roughness profile of about 0.01-3 microns (and all values and ranges therebetween).

In another and/or alternative non-limiting embodiment of the disclosure, there is provided an interbody implant device that has a resulting contact angle of from about 5-60° (and all values and ranges therebetween).

In another and/or alternative non-limiting embodiment of the disclosure, there is provided an interbody implant device that optionally includes a metallic coating on one or both of the frame structure and the porous structure.

In another and/or alternative non-limiting embodiment of the disclosure, there is provided an interbody implant device that does not include or utilize support struts within the 3D profile of the interbody implant device.

In another and/or alternative non-limiting embodiment of the disclosure, there is provided an interbody implant device that does int include support struts connected between the outer top and bottom rims, the rear plate and the top and bottom front plates, and the inner top rim and the inner bottom rim.

In another and/or alternative non-limiting embodiment of the disclosure, there is provided an interbody implant device that includes a porous material forming a porous structure that defines and supports substantially all the sidewalls.

In another and/or alternative non-limiting embodiment of the disclosure, there is provided an interbody implant device that includes a porous structure form of a plurality of voids or open pores and a plurality of webs which together form a pattern or lattice.

In another and/or alternative non-limiting embodiment of the disclosure, there is provided an interbody implant device that includes a porous structure that is a 3D printed structure made using any suitable additive manufacturing technique known in the art.

In another and/or alternative non-limiting embodiment of the disclosure, there is provided an interbody implant device that includes a porous material forming a porous structure that has an average density that is less than an average density of the body profile, the rear plate, the top front plate, the bottom front plate, the outer top rim, and/or the outer bottom rim.

In another and/or alternative non-limiting embodiment of the disclosure, there is provided an interbody implant device that uses various process parameters to form the 3D printed porous structure such that the plurality of pores and webs are not arranged in any particular order and the pattern is completely randomized, such that the randomized pattern of pores and webs is advantageous for mimicking the structure of cancellous bone.

In another and/or alternative non-limiting embodiment of the disclosure, there is provided an interbody implant device that includes a process that creates a porous structure having volumetric density which ranges from about 0.1 g/cm$^3$ to about 5 g/cm$^3$ (and all values and ranges therebetween).

In another and/or alternative non-limiting embodiment of the disclosure, there is provided an interbody implant device that includes a process that creates a porous structure having a series of overlapping layers in 3D space, resulting in a randomized pattern of voids and webs wherein: (a) the overlapping layers have an overlap of from about 5-100% (and all values and ranges therebetween); (b) voids in the porous material have a size of from about 0.001-0.5 in. (and all values and ranges therebetween); and/or (c) webs in the porous material have a thickness of from about 0.0005-0.1 in. (and all values and ranges therebetween).

In another and/or alternative non-limiting embodiment of the disclosure, there is provided an interbody implant device that includes a process that creates a porous structure having an Ra surface roughness which is the same or different from the Ra surface roughness of the frame structure.

In another and/or alternative non-limiting embodiment of the disclosure, there is provided an interbody implant device for use between bony structures and/or cartilage, wherein said interbody implant device has at least three unique surfaces making a 3D profile of said interbody implant device, said interbody implant device having a porous structure positioned at least partially within said 3D profile, said interbody implant device absent support struts on one or more sides.

In another and/or alternative non-limiting embodiment of the disclosure, there is provided an interbody implant device for use between bony structures and/or cartilage, wherein said interbody implant device has a top surface, a bottom surface, a front wall, a rear wall, a first side wall and a second side wall, said interbody implant device including a frame structure and a porous structure positioned at least partially within said frame structure, said frame structure including a rear plate, an outer top rim, an outer bottom rim, a top front plate and a bottom front plate, said rear plate forms at least a portion of said rear wall, said rear plate optionally includes a screw opening, said outer top rim forming an outer peripheral edge of said top surface, said outer top rim connected to said rear wall, said outer bottom rim forming an outer peripheral edge of said bottom surface, said outer bottom rim connected to said rear wall, said front wall including said top and bottom front plates, said top front plate connected to said outer top rim, said bottom front plate connected to said outer bottom rim, said top and bottom plates spaced from one another, said outer top and bottom rims spaced from one another, said rear plate spaced from said top and bottom front plates.

In another and/or alternative non-limiting embodiment of the disclosure, there is provided an interbody implant device for use between bony structures and/or cartilage, wherein said interbody implant device has a top surface, a bottom surface, a front wall, a rear wall, a first side wall and a second side wall, said interbody implant device including a frame structure and a porous structure positioned at least partially within said frame structure, said frame structure including a rear plate, an outer top rim, an outer bottom rim, said rear plate forms at least a portion of said rear wall, said rear plate optionally includes a screw opening, said outer top rim forming an outer peripheral edge of said top surface, said outer bottom rim forming an outer peripheral edge of said bottom surface, said outer top and bottom rims spaced from one another, said rear plate spaced from said top and bottom front plates, said outer top rim and said outer bottom rim is only connected to said rear plate and said porous structure.

In another and/or alternative non-limiting embodiment of the disclosure, there is provided an interbody implant device wherein said frame structure further includes a top front plate and a bottom front plate on said front wall, said top front plate connected to said outer top rim, said bottom front plate connected to said outer bottom rim, said top and bottom plates spaced from one another, said outer top and bottom rims spaced from one another, said rear plate spaced from said top and bottom front plates.

In another and/or alternative non-limiting embodiment of the disclosure, there is provided an interbody implant device wherein said porous material has an average density that is less than an average density of said profile, said rear plate, said top front plate, said bottom front plate, said outer top rim and/or said outer bottom rim.

In another and/or alternative non-limiting embodiment of the disclosure, there is provided an interbody implant device wherein said frame structure is absent struts within said 3D profile connected between said outer top rim and said outer bottom rim.

In another and/or alternative non-limiting embodiment of the disclosure, there is provided an interbody implant device wherein said frame structure is absent struts connected between said rear plate and said top front plate and/or said bottom front plate.

In another and/or alternative non-limiting embodiment of the disclosure, there is provided an interbody implant device wherein said rear plate forms less than 20% of the surface area of said rear wall.

In another and/or alternative non-limiting embodiment of the disclosure, there is provided an interbody implant device wherein said frame structure further includes an inner top rim and an inner bottom rim, said inner top rim and said inner bottom rim spaced from one another, said outer top rim spaced from said inner top rim, said outer bottom rim spaced from said inner bottom rim.

In another and/or alternative non-limiting embodiment of the disclosure, there is provided an interbody implant device wherein said frame structure is absent struts connected between said inner top rim and said inner bottom rim.

In another and/or alternative non-limiting embodiment of the disclosure, there is provided an interbody implant device wherein frame structure further includes a central opening, said inner top rim defines an upper perimeter of said central opening, said inner bottom rim defines a lower perimeter of said central opening.

In another and/or alternative non-limiting embodiment of the disclosure, there is provided an interbody implant device wherein said porous structure includes a randomized pattern of open pores.

In another and/or alternative non-limiting embodiment of the disclosure, there is provided an interbody implant device wherein said porous structure is a 3D printed structure.

In another and/or alternative non-limiting embodiment of the disclosure, there is provided an interbody implant device wherein said outer top rim and/or said outer bottom rim includes one or more surface serrations or teeth.

In another and/or alternative non-limiting embodiment of the disclosure, there is provided an interbody implant device wherein a bottom surface of said inner top rim is partially or fully absent said porous material to form an upper undercut in said central opening and/or a top surface of said inner bottom rim is partially or fully absent said porous material to form a lower undercut in said central opening.

In another and/or alternative non-limiting embodiment of the disclosure, there is provided an interbody implant device wherein said upper undercut in said central opening is 0.05 mm-15 mm (and all values and ranges therebetween) and/or said lower undercut in said central opening is 0.05-5 mm (and all values and ranges therebetween).

In another and/or alternative non-limiting embodiment of the disclosure, there is provided an interbody implant device wherein said porous material has a mass/volume ranging of 0.1-5 g/cm$^3$ (and all values and ranges therebetween).

In another and/or alternative non-limiting embodiment of the disclosure, there is provided an interbody implant device wherein said porous material is formed of a series of overlapping layers in 3D space resulting in a randomized pattern of voids and webs wherein a) the overlapping layers have an overlap of 5-100% (and all values and ranges therebetween), b) the voids in the porous material have a size of 0.001-0.5 in. (and all values and ranges therebetween), and/or c) the thickness of said webs is 0.0005-0.1 in (and all values and ranges therebetween).

In another and/or alternative non-limiting embodiment of the disclosure, there is provided an interbody implant device wherein said frame structure has outer surfaces having a Ra surface of 0.1-3 microns (and all values and ranges therebetween) as defined as the arithmetic average of a set of individual measurements of a surface's peaks and valleys.

In another and/or alternative non-limiting embodiment of the disclosure, there is provided an interbody implant device wherein said frame structure and/or said porous material includes a metallic coating.

In another and/or alternative non-limiting embodiment of the disclosure, there is provided an interbody implant device wherein metallic coating is formed by a thermal coating process, electroplating process, and/or CVD coating process.

In another and/or alternative non-limiting embodiment of the disclosure, there is provided an interbody implant device wherein metallic coating has a coating thickness of 0.000001-0.1 in (and all values and ranges therebetween).

In another and/or alternative non-limiting embodiment of the disclosure, there is provided an interbody implant wherein said structure has a resulting contact angle ranging of 5-60° (and all values and ranges therebetween).

In another and/or alternative non-limiting embodiment of the disclosure, there is provided a method of forming an interbody implant device for use between bony structures, the method comprising: 1) forming a frame structure, comprising i) forming a rear plate to define at least a portion of a rear wall of said orthopedic implant; ii) forming an outer top rim to define at least a portion of a top surface of said orthopedic implant and connecting said outer top rim to said rear wall; iii) forming an outer bottom rim spaced apart from said outer top rim to define at least a portion of a bottom surface of said orthopedic implant and connecting said outer bottom rim to said rear wall; iv) forming a top front plate and forming a bottom front plate spaced apart from said top front plate to define at least a portion of a front wall of said orthopedic implant and connecting said top front plate to said outer top rim and connecting said bottom front plate to said outer bottom rim; and 2) forming a porous structure positioned at least partially within said frame structure.

In another and/or alternative non-limiting embodiment of the disclosure, there is provided a method that further comprises forming an inner top rim and forming an inner bottom rim spaced apart from said inner top rim, wherein said inner top rim is spaced apart from said outer top rim and said inner bottom rim is spaced apart from said outer bottom rim.

In another and/or alternative non-limiting embodiment of the disclosure, there is provided a method that further comprises forming a central opening having an upper perimeter defined by said inner top rim and having a lower perimeter defined by said inner bottom rim.

In another and/or alternative non-limiting embodiment of the disclosure, there is provided a method that further comprises forming a metallic coating over said frame structure and/or said porous structure.

In another and/or alternative non-limiting embodiment of the disclosure, there is provided a method wherein forming said porous structure further comprises forming a randomized pattern of open pores.

In another and/or alternative non-limiting embodiment of the disclosure, there is provided a method wherein said forming said randomized pattern of open pores comprises using a Voronoi Lattice to generate a base lattice of said orthopedic implant by utilizing random seeds to break planar areas of said Voronoi Lattice based on a proximity of said random seeds to said planar areas.

In another and/or alternative non-limiting embodiment of the disclosure, there is provided a method that further comprises generating a surface roughness lattice for said base lattice by utilizing random seeds to form disconnected beam.

These and other advantages will become apparent from the following description taken together with the accompanying drawings.

BRIEF DESCRIPTION OF THE DRAWINGS

Reference may now be made to the drawings, which illustrate various nonlimiting embodiments that the disclosure may take in physical form and in certain parts and arrangement of parts wherein.

DETAILED DESCRIPTION

Figure 1:
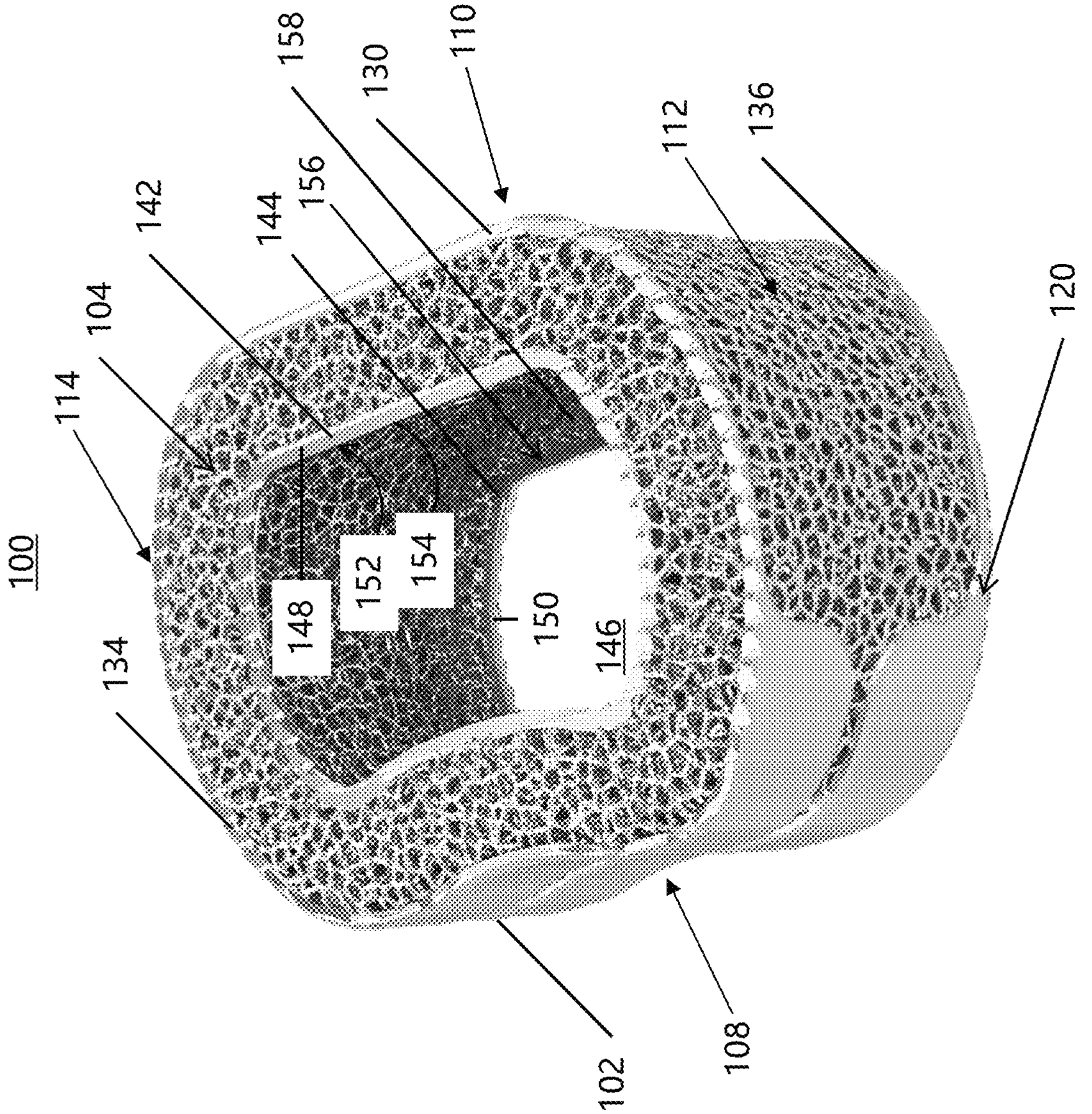
FIG. 1 is a side elevation view of one non-limiting embodiment of the present disclosure which illustrates an interbody implant device which includes a frame structure and a porous structure.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms “a,” “an,” and “the” include plural referents unless the context clearly dictates otherwise.

As used in the specification and in the claims, the term “comprising” may include the embodiments “consisting of” and “consisting essentially of” The terms “comprise(s),” “include(s),” “having,” “has,” “can,” “contain(s),” and variants thereof, as used herein, are intended to be open-ended transitional phrases, terms, or words that require the presence of the named ingredients/steps and permit the presence of other ingredients/steps. However, such description should be construed as also describing compositions or processes as “consisting of” and “consisting essentially of” the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of “from 2 grams to 10 grams” is inclusive of the endpoints, 2 grams and 10 grams, and all the intermediate values).

The terms “about” and “approximately” can be used to include any numerical value that can vary without changing the basic function of that value. When used with a range, “about” and “approximately” also disclose the range defined by the absolute values of the two endpoints, e.g. “about 2 to about 4” also discloses the range “from 2 to 4.” Generally, the terms “about” and “approximately” may refer to plus or minus 10% of the indicated number.

Percentages of elements should be assumed to be percent by weight of the stated element, unless expressly stated otherwise.

Embodiments of the disclosure are generally directed to intervertebral implants, systems, and method of use thereof. The interbody implant may be suitable for use with the anterior, antero-lateral, lateral, and/or posterior portions of at least one motion segment unit of the spine. Traditionally, interbody spacers or implants intended to help facilitate intervertebral fusion may serve to restore intervertebral height and/or lordosis. The interbody implants may feature a central lumen to house bone graft material, for example. It is through this central lumen where most of the fusion may occur.

The interbody implants of the disclosure may incorporate a volumetric, interconnected porosity throughout the entire spacer or a portion thereof. This enables bone to grow into and/or through the spacer or a portion thereof, making it part of the fusion mass. The incorporation of a volumetric, interconnected porosity may encourage faster, stronger intervertebral fusion, thereby providing for better patient outcomes.

Various forms of additive manufacturing, or 3D printing, have been developed which allow structures to be formed layer by layer. One illustrative 3D printing technology is Direct Metal Laser Sintering (DMLS) wherein parts are built using a laser to selectively sinter (heat and fuse) a powdered metal material into layers. The process begins once a 3D CAD file is mathematically sliced into multiple 2D cross sections and uploaded into the system. After the first layer is produced, the build platform is lowered, another powder layer is spread across the plate, and the laser sinters the second layer. This process is repeated until the part is complete. Layer-by-layer manufacturing allows for the direct fabrication of complex parts that would be cost-prohibitive, and often impossible, to produce through traditional manufacturing processes. The powder layer thickness used during the fabrication of the spacers may be as thin at 30 μm. The resolution of the laser may be as fine as 70 μm; however, it is envisioned that any suitable thickness or laser resolution may be used or selected.

The disclosure is not limited to DMLS; various 3D printing methods may be utilized. For example, VAT Photopolymerization utilizes a vat of liquid photopolymer resin which is cured through selective exposure to light (via a laser or projector) which then initiates polymerization and converts the exposed areas to a solid part. Powder Bed Fusion, of which DMLS is a subcategory, utilizes powdered materials which are selectively consolidated by melting together using a heat source such as a laser or electron beam. The powder surrounding the consolidated part acts as support material for overhanging features. Binder Jetting Liquid selectively applies bonding agents onto thin layers of powdered material to build up parts layer by layer. The binders include organic and inorganic materials. Metal or ceramic powdered parts are typically fired in a furnace after they are printed. Material Jetting deposits droplets of material layer by layer to make parts. Common varieties include jetting a photocurable resin and curing it with UV light, as well as jetting thermally molten materials that then solidify in ambient temperatures. In Sheet Lamination, sheets of material are stacked and laminated together to form an object. The lamination method can be adhesives or chemical (paper/plastics), ultrasonic welding, or brazing (metals). Unneeded regions are cut out layer by layer and removed after the object is built. Material Extrusion extrudes material through a nozzle or orifice in tracks or beads, which are then combined into multi-layer models. Common varieties include heated thermoplastic extrusion and syringe dispensing. Directed Energy Deposition feeds powder or wire into a melt pool which has been generated on the surface of the part where it adheres to the underlying part or layers by using an energy source such as a laser or electron beam.

The interbody implants of the disclosure may be manufactured from any of these or other additive manufacturing processes currently known or later developed. The interbody implants may also be manufactured utilizing a combination of additive manufacturing processes and other manufacturing processes, for example, laser etching. Additionally, the interbody implants may be further processed during and/or after manufacture utilizing various techniques, for example, abrasion, machining, polishing, or chemical treatment.

The interbody implants may be manufactured from various materials, such as biocompatible materials, including metals, polymers, ceramics or combinations thereof. Exemplary materials include metal materials (e.g., titanium, titanium alloys, cobalt-chrome alloys, stainless steel, molybdenum alloys, rhenium alloys, molybdenum-rhenium alloys, tungsten alloys, etc.) and polymers (e.g., PEEK, etc.).

Referring now to the drawings wherein the showings are for the purpose of illustrating non-limiting embodiments of the disclosure only and not for the purpose of limiting the same, FIGS. 1-7 illustrate a non-limiting embodiment of a lattice structure configured for use in the interbody implant device 100. The interbody implant device 100 is specially adapted for use between bony structures and generally includes at least six unique surfaces which define a body or 3D profile 102 of the interbody implant device 100. An external frame structure 120 and integral internal porous structure 160 structurally support the interbody implant device 100 such that the general shape of the 3D profile 102 and overall structural integrity can be maintained during the lifespan of the interbody implant device 100. In this regard, the porous structure 160 is generally positioned at least partially within the frame structure 150. Furthermore, the porous structure 160 can optionally be configured to extend to and to form at least a portion of each surface which defines the 3D profile 102.

The six unique surfaces which define the 3D profile 102 of the interbody implant device 100 include, but are not limited to, top and bottom surfaces 104, 106, front and rear walls 108, 110, and first and second sidewalls 112, 114 extending between the front and rear walls. The walls 108-114 are generally configured to place the top and bottom surfaces 104, 106 in spaced apart relation. The spacing between the top and bottom surfaces 104, 106 generally corresponds to the spacing of two bone/cartilage structures. For example, when the interbody implant device 100 is used as a spinal implant, the spacing between the top and bottom surfaces 104, 106 generally corresponds to the intervertebral spacing defined by the spinal disc and/or vertebral body to be replaced by the interbody implant device 100. To meet this end, the top and bottom surfaces 104, 106 each define and extend along separate planes which are oriented in relation to one another depending on the shape of the spinal disc and/or vertebral body to be replaced. In various non-limiting embodiments discussed herein, the top and bottom surfaces may generally be oriented along converging planes, diverging planes, and/or parallel planes.

Figure 5:
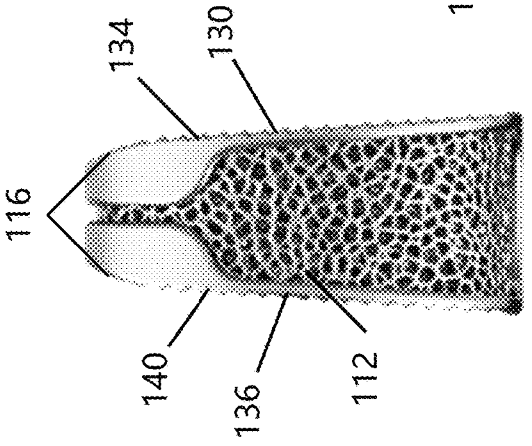
FIG. 5 is side plan view of the interbody implant device of FIG. 1.
Figure 6:
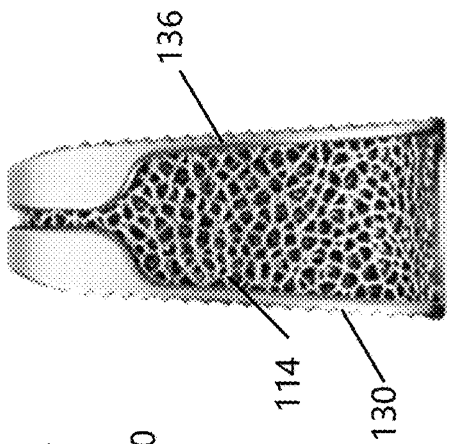
FIG. 6 is an opposite side plan view of the interbody implant device of FIG. 1.

As best seen in the left-side and right-side profile views of the interbody implant device 100 illustrated in FIGS. 5 and 6, the top and bottom surfaces 104, 106 of exemplary interbody implant device 100 extend from the rear wall 110 to the front wall 108 along converging planes. In other words, top and bottom surfaces 104, 106 are spaced apart a greatest distance at the rear wall 110 and a shortest distance at the front wall 108. However, as mentioned above, such a configuration is non-limiting.

Figure 4:
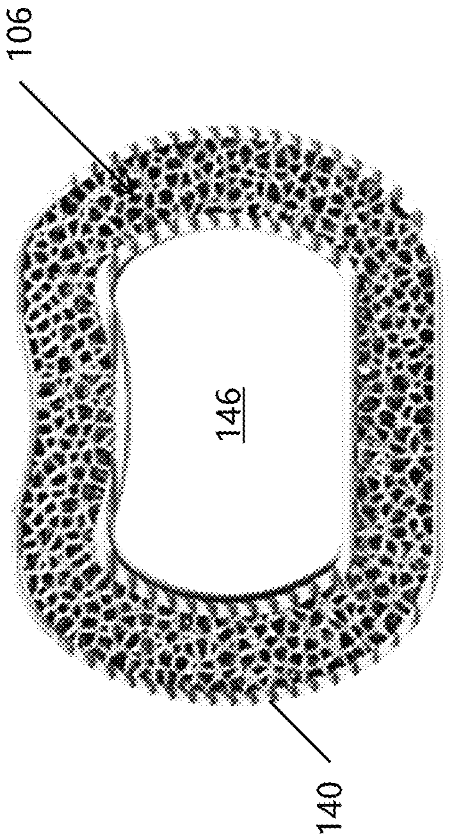
FIG. 4 is a bottom plan view of the interbody implant device of FIG. 1.

As also illustrated in FIG. 4, the side walls have a generally the same curved outer surface profile. As such the first side wall 112 and second side wall 114 are generally parallel to one another along the respective lengths of the side walls. The corresponding inner wall formed between inner top rim 142 and the inner bottom rim 144 has a generally corresponding shape to the respective first and second side walls 112, 114. The rear wall 110 has a generally straight or planar profile along over 50% the length of the rear wall, and typically has a generally straight or planar profile along over 75% the length of the rear wall. The front wall has a generally curved profile. As illustrated in FIG. 4, the front wall 108 initially curves generally downwardly and then curves upwardly along the length of the front wall.

In addition, the profile 102 of the interbody implant device 100 may include an optional smooth lead-in portion or optional taper 116 located adjacent the front wall 108 and formed by at least a portion of both top and bottom surfaces 104, 106. The taper 116 is configured to aid in the insertion of the interbody implant device 100 between the bone and/or cartilage.

The frame structure 120 illustrated in FIGS. 1-6 will now be described in further detail. In some particular non-limiting embodiments, the frame structure 120 is generally defined by a rear plate 122 spaced apart from top and bottom front plates 126, 128, outer top and bottom rims 130, 136, and inner top and bottom rims 142, 144. The top rim 130 is connected to the top of the rear plate 122 and to the top of front plate 126. The bottom rim 136 is connected to the bottom of the rear plate 122 and to the bottom of bottom plate 128.

Figure 3:
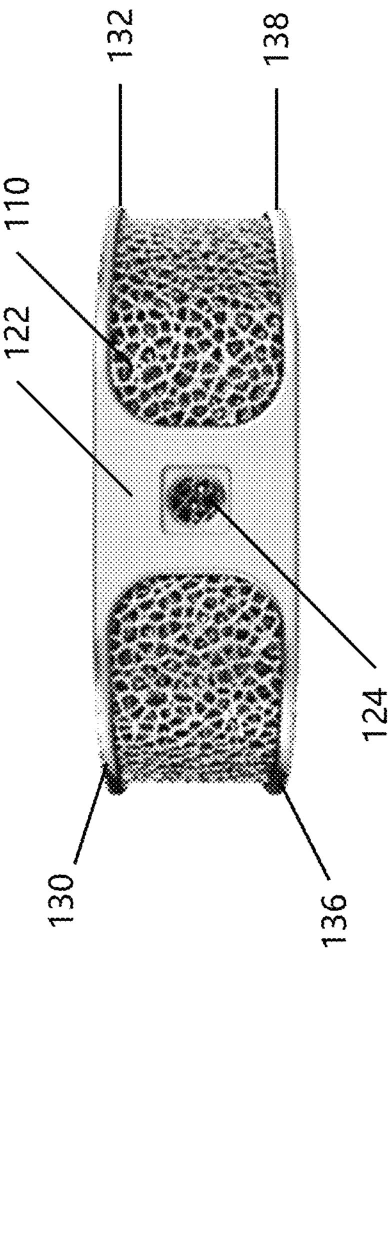
FIG. 3 is a rear plan view of the interbody implant device of FIG. 1.

As seen in FIG. 3, an aperture 124 optionally formed in the rear plate 122 provides a screw opening configured to provide a rigid connection with a tool or instrument used for inserting the implant device 100. The plate elements 122, 126, 128 and the rim elements 130, 136, 142, 144 are all generally connected to the porous structure 160, which is positioned at least partially within the frame structure 120. The outer top and bottom rims 130, 136 are spaced apart from one another and are each configured to provide at least one point of connection with the plate members 122, 126, and 128.

As seen in FIG. 3, the rear plate 122 extends fully between and connects to both the outer top rim 130 and outer bottom rim 136 on the rear wall 110. Generally, the rear plate is limited to the rear portion of the interbody implant device 100 as illustrated in FIG. 3; however, it can be appreciated that the rear wall 110 can optionally extend to a portion of one or both sides of the interbody implant device 100. As illustrated in FIG. 3, the rear wall 110 covers about 5-100% (and all values and ranges therebetween) of the rear surface of the interbody implant device 100, typically covers 10-65% of the rear surface of the interbody implant device 100, and more typically covers 30-60% of the rear surface of the interbody implant device 100. As also illustrated in FIG. 3, the rear wall 110 covers about 0-5% of one or both sides of the interbody implant device 100.

Figure 2:
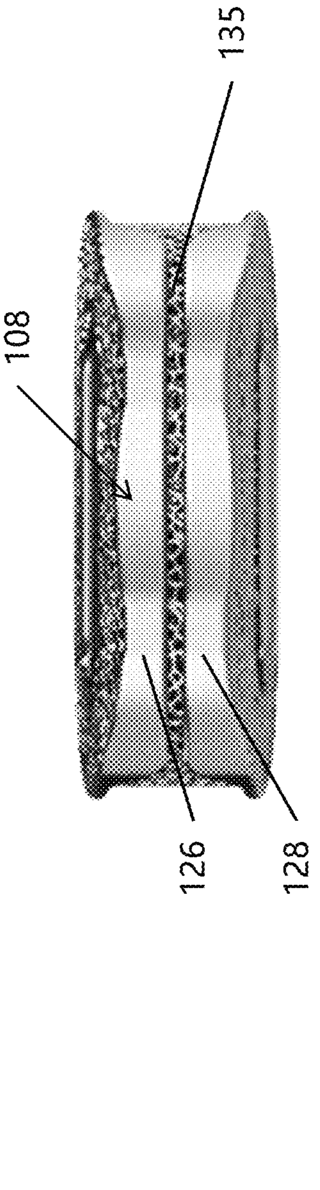
FIG. 2 is a front plan view of the interbody implant device of FIG. 1.

In FIG. 2, the top front plate 126 connects to the outer top rim 130 and the bottom front plate 128 connects to the outer bottom rim 136 on the front wall 108. The top and bottom front plates 126, 128 are also spaced from one another to form a front plate gap 135 on the front wall 108. The front plate gap 135 advantageously allows for the load applied to the porous structure 160, thereby reducing the stiffness of the body profile 102 of the interbody implant device 100. The top front plate 126 and bottom front plate 128 generally covers 15-98% (and all values and ranges therebetween) of the front surface of the interbody implant device 100, typically covers 25-95% of the front surface of the interbody implant device 100, and more typically covers 51-90% of the front surface of the interbody implant device 100. As illustrated in FIGS. 1, 2, 5 and 6, the top and/or bottom front plates 130, 136 can optionally form a portion of one or both sides of the interbody implant device 100. In one specific non-limiting arrangement, the top and/or bottom front plates 130, 136 can optionally form 0-60% (and all values and ranges therebetween) of one or both sides of the interbody implant device 100, typically the top and/or bottom front plates 130, 136 can optionally form 0-45% of one or both sides of the interbody implant device 100, and more typically the top and/or bottom front plates 130, 136 can optionally form 0-30% of one or both sides of the interbody implant device 100.

With reference to FIGS. 1 and 4, the outer top rim 130 forms an outer peripheral edge 132 of the top surface 104 and the outer bottom rim 136 forms an outer peripheral edge 138 of the bottom surface 106. Generally, the outer top rim 130 and the outer bottom rim 136 are formed of smooth surfaces to reduce or eliminate any sharp outer peripheral surfaces on the outer top rim 130 and/or the outer bottom rim 136; however, this is not required. In FIG. 2, the top front plate 126 forms at least part of an upper portion of the front wall 108 and the bottom front plate 128 forms at least part of a lower portion of the front wall. The front plate gap 135 generally is located ±0-10% (and all values and ranges therebetween) of the central longitudinal axis or plane of the interbody implant device 100, and typically the front plate gap 135 generally is located ±0-5% of the central longitudinal axis or plane of the interbody implant device 100. The outer top rim 130 and/or the outer bottom rim 136 can optionally form a portion of the back surface of the interbody implant device 100 interbody implant device 100. Generally, the outer top rim 130 and/or the outer bottom rim 136 forms 0-30% (and all values and ranges therebetween) of the back surface of the interbody implant device 100, typically the outer top rim 130 and/or the outer bottom rim 136 forms 0-15% of the back surface of the interbody implant device 100, and more typically the outer top rim 130 and/or the outer bottom rim 136 forms 0-10% of the back surface of the interbody implant device 100. As illustrated in FIG. 3, the outer top rim 130 and/or the outer bottom rim 136 forms about 3-8% of the back surface of the interbody implant device 100. The outer top rim 130 and/or the outer bottom rim 136 can optionally form a portion of the front surface of the interbody implant device 100. Generally, the outer top rim 130 and/or the outer bottom rim 136 forms 0-20% (and all values and ranges therebetween) of the front surface of the orthopedic implant device 100, typically the outer top rim 130 and/or the outer bottom rim 136 forms 0-10% of the front surface of the interbody implant device 100, and more typically the outer top rim 130 and/or the outer bottom rim 136 forms 0-5% of the front surface of the interbody implant device 100. As illustrated in FIGS. 1, 2, 5 and 6, the outer top rim 130 and/or the outer bottom rim 136 forms 0% of the front surface of the interbody implant device 100. The outer top rim 130 and/or the outer bottom rim 136 form a portion of the one or both side surfaces of the interbody implant device 100. Generally, the outer top rim 130 and/or the outer bottom rim 136 forms 1-60% (and all values and ranges therebetween) of one or both side surfaces of the interbody implant device 100, typically the outer top rim 130 and/or the outer bottom rim 136 forms 2-40% of one or both side surfaces one or both side surfaces of the interbody implant device 100, and more typically the outer top rim 130 and/or the outer bottom rim 136 forms 3-10% of one or both side surfaces of the interbody implant device 100. As illustrated in FIGS. 1, 2, 5 and 6, the outer top rim 130 and/or the outer bottom rim 136 forms about 3-8% of each of the side surfaces of the interbody implant device 100.

In some non-limiting embodiments, the top and bottom front plates 126, 128 are optional. In such embodiments, the outer top rim and outer bottom rim is only connected to the rear plate and the porous structure.

In other non-limiting embodiments, the sidewalls 112, 114 are configured to be generally open. That is, no portion of the frame structure 120 provides support to the sidewalls 112/114. Rather, the sidewalls 112, 114 are composed entirely of the porous material of porous structure 160. However, such a configuration is non-limiting.

In other non-limiting embodiments, the sidewalls 112, 114 are configured to be substantially open. That is, only the outer top rim 130 and/or the outer bottom rim 136 form a portion of the one or both side surfaces of the interbody implant device 100.

Generally, the outer top rim 130 and/or the outer bottom rim 136 in this non-limiting embodiment forms 1-10% (and all values and ranges therebetween) of one or both side surfaces of the interbody implant device 100. However, such a configuration is non-limiting.

In some particular non-limiting embodiments, the rear wall 110 has a surface area and the rear plate 122 forms less than about 50% of the rear wall surface area. In one non-limiting configuration, the rear plate 122 forms less than about 10-30% of the rear wall surface area, and generally no more than about 20%. However, such a configuration is non-limiting.

In some non-limiting embodiments, one or more surface serrations or teeth 134 are formed on the outer top rim 130. In addition or alternatively, the outer bottom rim 136 can have one or more surface serrations or teeth 140 formed thereon. The one or more surface serrations or teeth 134, 140 are best seen in FIGS. 5 and 6 and are generally configured to help prevent the interbody implant device 100 from backing out after the device has been inserted. However, such a configuration is non-limiting.

As best seen in FIGS. 1 and 4, the inner top and bottom rims 142, 144 are spaced apart from one another. Moreover, the inner top and bottom rims 142, 144 are spaced apart from the outer top and bottom rims 130, 136, respectively. In some embodiments, the inner top and bottom rims 142, 144 are spaced in a concentric manner to the outer top and bottom rims 130, 136, respectively. As illustrated in FIG. 1, the thickness of the inner top rim 142 is about 1-40% (and all values and ranges therebetween) the maximum width between the inner top rim 142 and the outer top rim 130, and typically the thickness of the inner top rim 142 is about 2-15% the maximum width between the inner top rim 142 and the outer top rim 130. As illustrated in FIG. 1, the thickness of the outer top rim 130 is about 1-40% (and all values and ranges therebetween) the maximum width between the inner top rim 142 and the outer top rim 130, and typically the thickness of the outer top rim 130 is about 2-15% the maximum width between the inner top rim 142 and the outer top rim 130. As illustrated in FIG. 4, the thickness of the inner bottom rim 144 is about 1-40% (and all values and ranges therebetween) the maximum width between the inner bottom rim 144 and the outer bottom rim 136, and typically the thickness of the inner bottom rim 144 is about 2-15% the maximum width between the inner bottom rim 144 and the outer bottom rim 136. As illustrated in FIG. 4, the thickness of the outer bottom rim 136 is about 1-40% (and all values and ranges therebetween) the maximum width between the inner bottom rim 144 and the outer bottom rim 136, and typically the thickness of the outer bottom rim 136 is about 2-15% the maximum width between the inner bottom rim 144 and the outer bottom rim 136.

As best seen in FIGS. 5 and 6, the outer top and bottom rims 130, 136 are spaced apart from one another. The width/height of the outer top rim 130 is about 1-40% (and all values and ranges therebetween) the maximum width/height between the outer top rim 130 and the outer bottom top rim 136, and typically the width/height of the outer top rim 130 is about 2-15% the maximum width/height between the outer top rim 130 and the outer bottom top rim 136. The width/height of the outer bottom rim 136 is about 1-40% (and all values and ranges therebetween) the maximum width/height between the outer top rim 130 and the outer bottom top rim 136, and typically the width/height of the outer bottom rim 136 is about 2-15% the maximum width/height between the outer top rim 130 and the outer bottom top rim 136.

The spaced apart relationship between each of the outer top rim 130, outer bottom rim 136, inner top rim 142, and inner bottom rim 144 provides the interbody implant device 100 with a profile 102 which is generally toroidal in shape. However, such a configuration is non-limiting.

With continued reference to FIGS. 1 and 4, the frame structure 120 further includes a central opening 146 defined within an inner perimeter of the body profile 102. The central opening 146 has an upper perimeter 148 defined by the inner top rim 142 and a lower perimeter 150 defined by the inner bottom rim 144. The central opening 146 is generally configured to receive one or more materials including, but not limited to, bone growth-promoting materials, drugs, and cartilage, for example. Generally, the cross-sectional size of the central opening 146 is at least 10% of the cross-sectional size of the interbody implant device 100. As illustrated in FIG. 4, the size of the cross-sectional size of the central opening 146 at the bottom surface 106 is about 10-80% (and all values and ranges therebetween) of the cross-sectional size of the bottom surface 106 of interbody implant device 100, and typically the size of the cross-sectional size of the central opening 146 at the bottom surface 106 is about 30-70% of the cross-sectional size of the bottom surface 106 of interbody implant device 100. As illustrated in FIG. 1, the size of the cross-sectional size of the central opening 146 at the top surface 104 is about 10-80% (and all values and ranges therebetween) of the cross-sectional size of the top surface 104 of interbody implant device 100, and typically the size of the cross-sectional size of the central opening 146 at the top surface 104 is about 30-70% of the cross-sectional size of the top surface 104 of interbody implant device 100.

Moreover, as best seen in FIG. 1, a bottom surface 152 of the inner top rim 142 and a top surface 156 of the inner bottom rim 144 are partially or fully absent the porous material which forms the porous structure 160. In this regard, an upper undercut 154 is optionally formed in the central opening 146 at the bottom surface 152 of inner top rim 142 due to the at least partial void of porous material. Similarly, a lower undercut 158 is also formed in the central opening 146 at the top surface 156 of inner bottom rim 144 due to the at least partial void of porous material. The upper and lower undercuts 154, 158 thus increase the amount of material which can be packed into the central opening 146. In one non-limiting embodiment, the width of the upper undercut 154 (when formed) is 5-99.5% (and all values and ranges therebetween) the width of the inner top rim 142, and typically the width of the upper undercut 154 (when formed) is 55-99.5% the width of the inner top rim 142. In one non-limiting embodiment, the width of the lower undercut 158 (when formed) is 5-99.5% (and all values and ranges therebetween) the width of the inner bottom rim 144, and typically the width of the lower undercut 158 (when formed), is 55-99.5% the width of the inner bottom rim 144.

In some particular non-limiting embodiments, the upper undercut 154 extends inward relative to the central opening 146 a distance of from about 0.05 mm to about 15 mm (and all values and ranges therebetween). In other embodiments, the lower undercut 156 extends into the central opening 146 a distance of from about 0.05 mm to about 5 mm. However, such configurations are non-limiting.

In some non-limiting embodiments, the frame structure 120 is formed to provide outer surfaces having an Ra roughness profile, or arithmetic mean roughness. Ra or arithmetic mean roughness is determined by the average of a set of peaks and valleys on a surface. In some embodiments, the outer surfaces of frame structure 120 has a roughness Ra of from about 0.01-3 microns (and all values and ranges therebetween), and typically the outer surfaces of frame structure 120 has a roughness Ra of from about 0.1-1 micron.

In other non-limiting embodiments, the peaks and valleys which define the Ra surface roughness described above also define a resulting contact angle between the frame structure 120 and adjacent spinal discs and/or vertebral bodies when the device 100 is inserted. The resulting contact angle is generally configured to promote bone growth, and the contact angle is directly proportional to the Ra surface roughness. Thus, when the Ra surface roughness increases, so does the contact angle, and vice versa. In some embodiments, the frame structure 120 has a resulting contact angle of from about 5-60° (and all values and ranges therebetween), and typically the frame structure 120 has a resulting contact angle of from about 10-40°. However, such a configuration is non-limiting.

In some non-limiting embodiments, a metallic coating is optionally applied to one or both of the frame structure 120 and porous structure 160. The metallic coating can optionally be formed by any one of a thermal coating process, electroplating process, and/or CVD coating process known in the art. In some embodiments, the metallic coating has a thickness of from about 0.000001-0.1 in. (and all values and ranges therebetween), and typically 0.00001-0.02 in. In other non-limiting embodiments, the metallic coating can be made from a metal or metal alloy. Some non-limiting examples of suitable materials for the metallic coating include but are not limited to a molybdenum alloy, rhenium alloy, molybdenum-rhenium alloy, titanium alloy, etc.

Notably, the frame structure 120 typically does not include or utilize support struts within the 3D profile 102 of the interbody implant device. Specifically, no support struts are connected between the outer top and bottom rims 130, 136, the rear plate 122 and the top and bottom front plates 126/128, and the inner top rim 142 and the inner bottom rim 144.

The porous structure 160 of the exemplary interbody implant device 100 will now be described in further detail. As previously mentioned above, the porous material of the porous structure 160 extends to and forms at least a portion of each surface 104, 106, 108, 110, 112, and 114. As shown in FIGS. 1 and 4, the porous material of the porous structure 160 can be seen extending to and forming an inner annular portion of the top and bottom surfaces 104/106, respectively. As shown in FIG. 2, the porous material of the porous structure 160 extends to and forms central and upper portions of the front wall 108. As shown in FIG. 3, the porous material of the porous structure 160 extends to and forms side portions of the rear wall 110. Finally, as shown in FIGS. 5 and 6, the porous material of the porous structure 160 extends to and forms substantially all of each sidewall 112, 114, respectively. In other words, as mentioned above, the sidewalls 112, 114 are configured to be generally open, such that none of the frame structure 120 supports sidewalls 112, 114. Rather, the porous material of porous structure 160 defines and supports substantially all the sidewalls 112, 114. However, such a configuration is non-limiting.

Figure 7:
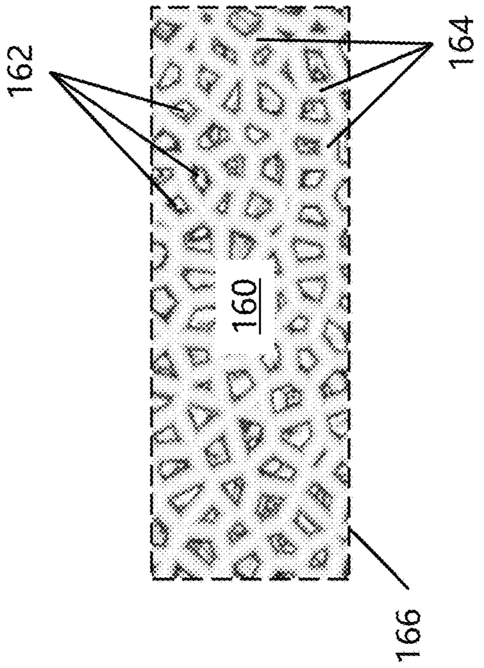
FIG. 7 is an enlarged view of a section of the internal porous structure of the interbody implant device of FIG. 1.

With reference to FIG. 7, the porous structure 160 includes a plurality of voids or open pores 162 and a plurality of webs 164 which together form a pattern or lattice 166. In accordance with some non-limiting embodiments, the porous structure 160 is a 3D printed structure made using any suitable additive manufacturing technique known in the art. In other non-limiting embodiments, the porous material forming the porous structure 160 has an average density that is less than an average density of the body profile 102, the rear plate 122, the top front plate 126, the bottom front plate 128, the outer top rim 130, and/or the outer bottom rim 136.

In one non-limiting configurations, the interbody implant device 100 is the form of a cervical interbody. The cervical interbody can be formed of a titanium alloy. The cervical interbody can have a footprints: 12 mm×12 mm, 14 mm×12 mm, and 16 mm×14 mm; however, other footprints can be used. The height can be 6-12 mm (and all values and ranges therebetween); however, other lengths can be used. The lordosis can be 6° and 10° (and all values and ranges therebetween); however, other lordosis can be used. The cervical interbody can have a smooth lead in on distal portion of the cervical interbody to aid in insertion. The cervical interbody has a random lattice structure with 300-500 micron pores (and all values and ranges therebetween); however, other pore sizes can be used. The lattice structure is configured to mimic cancellous bone. The cervical interbody includes surface serrations or teeth to help prevent the cervical interbody from backing out after the cervical interbody has been inserted between the bone/cartilage. The cervical interbody has a rough lattice structure that contacts the end plates to allow for initial stabilization. The cervical interbody has an inner pocket that is undercut in the lattice structure to increase the amount of bone graft and/or other material that can be packed into the cervical interbody. The load paths are configured to pass though the lattice structure to lower the overall stiffness of the cervical interbody. The front of the cervical interbody contains a gap that allows for the load that is applied to the lattice structure reduces the stiffness of the cervical interbody. The cervical interbody includes a threaded insertion feature to allow for rigid connection to an inserter.

Figure 9:
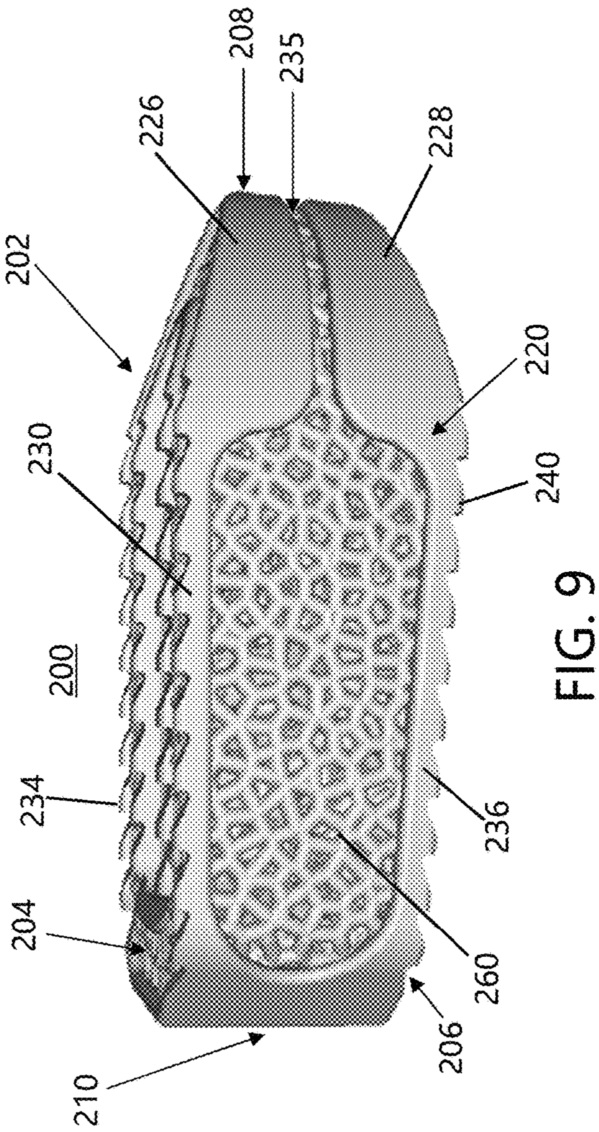
FIG. 9 side plan view of the interbody implant device of FIG. 8.
Figure 8:
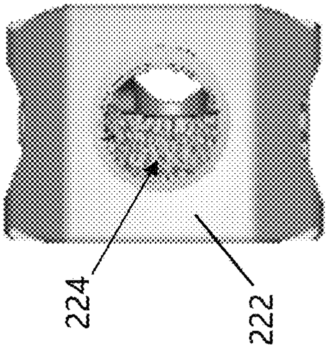
FIG. 8 is a rear plan view of the interbody implant device of another non-limiting embodiment of the present disclosure which illustrates an interbody implant device which includes a frame structure and a porous structure.
Figure 10:
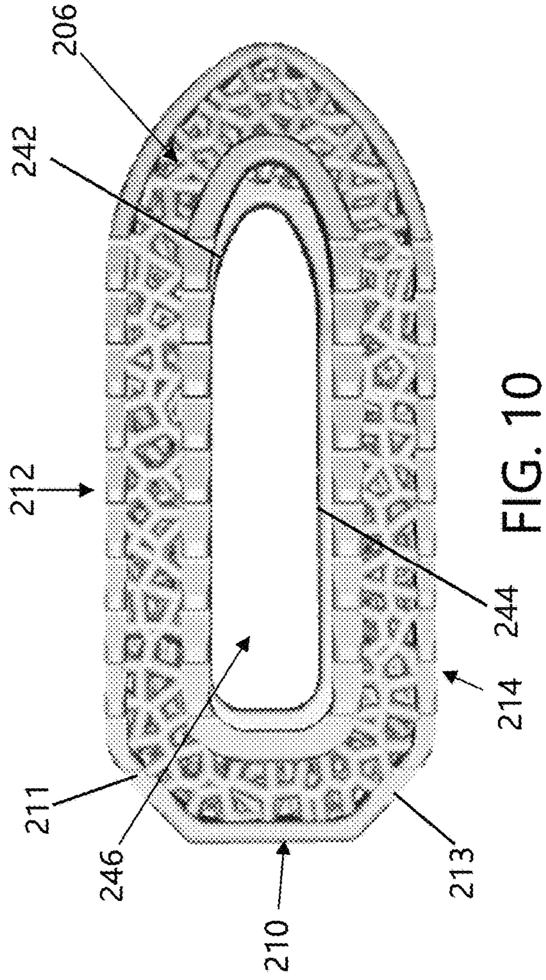
FIG. 10 is a bottom plan view of the interbody implant device of FIG. 8.

Referring now to FIGS. 8-10, another non-limiting interbody implant device 200 in the form of a PLIF interbody implant device is described. Many of the features of the interbody implant device 200 are the same or substantially similar to interbody implant device 100 as discussed above, thus will not be repeated herein. As illustrated in FIGS. 8-10, the shape of interbody implant device 200 is different from interbody implant device 100. The different shape allows interbody implant device 200 to be inserted in different shaped shapes between bone and/or cartilage.

The interbody implant device 200 is specially adapted for use between bony structures and generally includes at least six unique surfaces which define a body or 3D profile 202 of the interbody implant device 200. An external frame structure 220 and integral internal porous structure 260 structurally support the interbody implant device 200 such that the general shape of the 3D profile 202 and overall structural integrity can be maintained during the lifespan of the interbody implant device 200. The porous structure 260 is generally positioned at least partially within the frame structure. Furthermore, the porous structure 260 can optionally be configured to extend to and to form at least a portion of each surface which defines the 3D profile 202.

The six unique surfaces which define the 3D profile 202 of the interbody implant device 200 include, but are not limited to, top and bottom surfaces 204, 206, front and rear walls 208, 210, and first and second sidewalls 212, 214 extending between the front and rear walls. The walls 208-214 are generally configured to place the top and bottom surfaces 204, 206 in spaced apart relation. In various non-limiting embodiments discussed herein, the top and bottom surfaces may generally be oriented along converging planes, diverging planes, and/or parallel planes.

The top and bottom surfaces 204, 206 extend from the rear wall 210 to the front wall 208 along both converging and diverging planes. As best illustrated in FIG. 9, the top and bottom surfaces 204, 206 moving from the rear wall 210 to the front wall 208 initially are in diverging planes about 30-95% (and all values and ranges therebetween) of the longitudinal length of the interbody implant device 200, and typically the rear wall 210 to the front wall 208 initially are in diverging planes about 55-90% of the longitudinal length of the interbody implant device 200. Thereafter, the top and bottom surfaces 204, 206 lie in converging planes. In other words, top and bottom surfaces 204, 206 are spaced apart a greatest distance at a location between the rear wall 210 and the front wall 208. However, as mentioned above, such a configuration is non-limiting. The rear wall 210 has a generally straight or planar profile along over 50% the length of the rear wall. The two side portions 211, 213 of the rear wall 210 can optionally be tapered. The front wall 208 has a generally curved profile. As illustrated in FIG. 10, the front wall 208 initially curves generally upwardly and then curves downwardly along the length of the front wall.

As also illustrated in FIG. 10, the side walls have a generally straight or planar outer surface profile. As such the first side wall 212 and second side wall 214 are generally parallel to one another along over 50% of the longitudinal length of the interbody implant device 200. The corresponding inner wall formed between inner top rim 242 and the inner bottom rim 244 has a generally corresponding shape to the respective first and second side walls 212, 214.

In addition, the profile 202 of the interbody implant device 200 may include an optional smooth lead-in portion or optional taper located adjacent the front wall 208 and formed by at least a portion of both top and bottom surfaces 204, 206. The taper (when used) is configured to aid in the insertion of the interbody implant device 200 between the bone and/or cartilage.

The frame structure 220 illustrated in FIGS. 8-10 will now be described in further detail. In some particular non-limiting embodiments, the frame structure 220 is generally defined by a rear plate 222 spaced apart from top and bottom front plates 226, 228, outer top and bottom rims 230, 236, and inner top and bottom rims 242, 244. The top rim 230 is connected to the top of the rear plate 222 and to the top of front plate 226. The bottom rim 236 is connected to the bottom of the rear plate 222 and to the bottom of bottom plate 228.

As seen in FIG. 8, an aperture 224 optionally formed in the rear plate 222 provides a screw opening configured to provide a rigid connection with a tool or instrument used for inserting the implant device 200. The plate elements 222, 226, 228 and the rim elements 230, 236, 242, 244 are all generally connected to the porous structure 260, which is positioned at least partially within the frame structure 220. The outer top and bottom rims 230, 236 are spaced apart from one another and are each configured to provide at least one point of connection with the plate members 222, 226, and 228.

As illustrated in FIG. 8, the rear plate 222 extends fully between and connects to both the outer top rim 230 and outer bottom rim 236 on the rear wall 210. As illustrated in FIG. 8, the rear plate 222 forms substantially (80-100% and all values and ranges therebetween) the full rear portion of the interbody implant device 200. As illustrated in FIG. 9, the rear wall 210 can optionally extend to a portion of one or both sides of the interbody implant device 200. As illustrated in FIG. 9, the rear wall 210 covers about 0-25% (and all values and ranges therebetween) of one or both sides of the interbody implant device 200, and typically the rear wall 210 covers about 1-10% of one or both sides of the interbody implant device 200.

As illustrated in FIG. 9, the top front plate 226 connects to the outer top rim 230 and the bottom front plate 228 connects to the outer bottom rim 236 on the front wall 208. The top and bottom front plates 226, 228 are also spaced from one another to form a front plate gap 235 on the front wall 208. The front plate gap 235 advantageously allows for the load applied to the porous structure 260, thereby reducing the stiffness of the body profile 202 of the interbody implant device 200. The top front plate 226 and bottom front plate 228 generally covers 15-98% (and all values and ranges therebetween) of the front surface of the interbody implant device 200, and typically covers 51-95% of the front surface of the interbody implant device 200. The top and/or bottom front plates 230, 236 can optionally form a portion of one or both sides of the interbody implant device 200. In one specific non-limiting arrangement, the top and/or bottom front plates 230, 236 can optionally form 0-60% (and all values and ranges therebetween) of one or both sides of the interbody implant device 200, and typically the top and/or bottom front plates 230, 236 can optionally form 1-45% of one or both sides of the interbody implant device 200.

The outer top rim 230 forms an outer peripheral edge of the top surface 204 and the outer bottom rim 236 forms an outer peripheral edge of the bottom surface 206. Generally, the outer top rim 230 and the outer bottom rim 236 are formed of smooth surfaces to reduce or eliminate any sharp outer peripheral surfaces on the outer top rim 230 and/or the outer bottom rim 236; however, this is not required.

As illustrated in FIG. 9, the top front plate 226 forms at least part of an upper portion of the front wall 208 and the bottom front plate 228 forms at least part of a lower portion of the front wall. The front plate gap 235 generally is located ±0-10% (and all values and ranges therebetween) of the central longitudinal axis or plane of the interbody implant device 200, and typically the front plate gap 235 generally is located ±0-5% of the central longitudinal axis or plane of the interbody implant device 200. The outer top rim 230 and/or the outer bottom rim 236 can optionally form a portion of the back surface of the interbody implant device 200. Generally, the outer top rim 230 and/or the outer bottom rim 236 forms 0-30% (and all values and ranges therebetween) of the back surface of the interbody implant device 200, and typically the outer top rim 230 and/or the outer bottom rim 236 forms 0-15% of the back surface of the interbody implant device 200. The outer top rim 230 and/or the outer bottom rim 236 can optionally form a portion of the front surface of the interbody implant device 200. Generally, the outer top rim 230 and/or the outer bottom rim 236 forms 0-20% (and all values and ranges therebetween) of the front surface of the interbody implant device 200, and typically the outer top rim 230 and/or the outer bottom rim 236 forms 0-10% of the front surface of the interbody implant device 200. The outer top rim 230 and/or the outer bottom rim 236 typically forms a portion of the one or both side surfaces of the interbody implant device 200. Generally, the outer top rim 230 and/or the outer bottom rim 236 forms 1-60% (and all values and ranges therebetween) of one or both side surfaces of the interbody implant device 200, and typically the outer top rim 230 and/or the outer bottom rim 236 forms 2-40% of one or both side surfaces one or both side surfaces of the interbody implant device 200.

In some non-limiting embodiments, one or more surface serrations or teeth 234 are formed on the outer top rim 230. In addition or alternatively, the outer bottom rim 236 can have one or more surface serrations or teeth 240 formed thereon. The one or more surface serrations or teeth 234, 240 (best seen in FIG. 9) are generally configured to help prevent the interbody implant device 200 from backing out after the device has been inserted. However, such a configuration is non-limiting.

The inner top and bottom rims 242, 244 are spaced apart from one another. Moreover, the inner top and bottom rims 242, 244 are spaced apart from the outer top and bottom rims 230, 236, respectively. In some particular non-limiting embodiments, the inner top and bottom rims 242/244 are spaced in a concentric manner to the outer top and bottom rims 230, 236, respectively. The thickness of the inner top rim 242 is about 1-40% (and all values and ranges therebetween) the maximum width between the inner top rim 242 and the outer top rim 230, and typically the thickness of the inner top rim 242 is about 2-15% the maximum width between the inner top rim 242 and the outer top rim 230. The thickness of the outer top rim 230 is about 1-40% (and all values and ranges therebetween) the maximum width between the inner top rim 242 and the outer top rim 230, and typically the thickness of the outer top rim 230 is about 2-15% the maximum width between the inner top rim 242 and the outer top rim 230. The thickness of the inner bottom rim 244 is about 1-40% (and all values and ranges therebetween) the maximum width between the inner bottom rim 244 and the outer bottom rim 236, and typically the thickness of the inner bottom rim 244 is about 2-15% the maximum width between the inner bottom rim 244 and the outer bottom rim 236. The thickness of the outer bottom rim 236 is about 1-40% (and all values and ranges therebetween) the maximum width between the inner bottom rim 244 and the outer bottom rim 236, and typically the thickness of the outer bottom rim 236 is about 2-15% the maximum width between the inner bottom rim 244 and the outer bottom rim 236.

As best seen in FIG. 9, the outer top and bottom rims 230, 236 are spaced apart from one another. The width/height of the outer top rim 230 is about 1-40% (and all values and ranges therebetween) the maximum width/height between the outer top rim 230 and the outer bottom top rim 236, and typically the width/height of the outer top rim 230 is about 2-15% the maximum width/height between the outer top rim 230 and the outer bottom top rim 236. The width/height of the outer bottom rim 236 is about 1-40% (and all values and ranges therebetween) the maximum width/height between the outer top rim 230 and the outer bottom top rim 236, and typically the width/height of the outer bottom rim 236 is about 2-15% the maximum width/height between the outer top rim 230 and the outer bottom top rim 236.

With continued reference to FIG. 10, the frame structure 220 further includes a central opening 246 defined within an inner perimeter of the body profile 202. The central opening 246 has an upper perimeter defined by the inner top rim 242 and a lower perimeter defined by the inner bottom rim 244. The central opening 246 is generally configured to receive one or more materials including, but not limited to, bone growth-promoting materials, drugs, and cartilage, for example. Generally, the cross-sectional size of the central opening 246 is at least 10% of the cross-sectional size of the interbody implant device 200. As illustrated in FIG. 10, the size of the cross-sectional size of the central opening 246 at the bottom surface 206 is about 5-80% (and all values and ranges therebetween) of the cross-sectional size of the bottom surface 206 of interbody implant device 200, and typically the size of the cross-sectional size of the central opening 246 at the bottom surface 206 is about 10-70% of the cross-sectional size of the bottom surface 206 of interbody implant device 200. The size of the cross-sectional size of the central opening 246 at the top surface 204 is about 5-80% (and all values and ranges therebetween) of the cross-sectional size of the top surface 204 of interbody implant device 200, and typically the size of the cross-sectional size of the central opening 246 at the top surface 204 is about 10-70% of the cross-sectional size of the top surface 204 of interbody implant device 200.

As best seen in FIG. 10, a bottom surface of the inner top rim 242 and a top surface of the inner bottom rim 244 are optionally partially or fully absent the porous material which forms the porous structure 260. In this regard, an upper undercut is optionally formed in the central opening 246 at the bottom surface of inner top rim 242 due to the at least partial void of porous material. Similarly, a lower undercut is also optionally formed in the central opening 246 at the top surface of inner bottom rim 244 due to the at least partial void of porous material. The upper and lower undercuts (when formed) thus increase the amount of material which can be packed into the central opening 246. In one non-limiting embodiment, the width of the upper undercut (when formed) is 5-99.5% (and all values and ranges therebetween) the width of the inner top rim 242. In one non-limiting embodiment, the width of the lower undercut (when formed) is 5-99.5% (and all values and ranges therebetween) the width of the inner bottom rim 244. In some embodiments, the upper/lower undercut extends inward relative to the central opening 246 a distance of from about 0.05-15 mm (and all values and ranges therebetween).

In some non-limiting embodiments, the frame structure 220 is formed to provide outer surfaces having an Ra roughness profile or arithmetic mean roughness. In some embodiments, the outer surfaces of frame structure 220 has a roughness Ra of from about 0.01-3 micron (and all values and ranges therebetween). In some embodiments, the frame structure 220 has a resulting contact angle of from about 5-60° (and all values and ranges therebetween).

A metallic coating is optionally applied to one or both of the frame structure 220 and porous structure 260. The metallic coating has a thickness of from about 0.000001-0.1 in. (and all values and ranges therebetween).

The frame structure 220 typically does not include or utilize support struts within the 3D profile 202 of the interbody implant device. Specifically, no support struts are connected between the outer top and bottom rims 230, 236, the rear plate 222 and the top and bottom front plates 226, 228, and the inner top rim 242 and the inner bottom rim 244.

The porous material of the porous structure 260 extends to and forms at least a portion of each surface 204, 206, 208, 210, 212, and 214. The porous structure 260 includes a plurality of voids or open pores and a plurality of webs which together form a pattern or lattice. In accordance with some non-limiting embodiments, the porous structure 260 is a 3D printed structure made using any suitable additive manufacturing technique known in the art. In some other non-limiting embodiments, the porous material forming the porous structure 260 has an average density that is less than an average density of the body profile 202, the rear plate 222, the top front plate 226, the bottom front plate 228, the outer top rim 230, and/or the outer bottom rim 236.

Interbody implant device 200 is an example of a PLIF interbody. The interbody implant device 200 can be formed of titanium alloy; however, other materials can be used. The lattice structure has dimensions of 24 mm, 28 mm, and 32 mm; however, other lengths can be used. The height can be 8-14 mm; however, other heights can be used. The lordosis can be 5°; however, other lordosis can be used.

Figure 11:
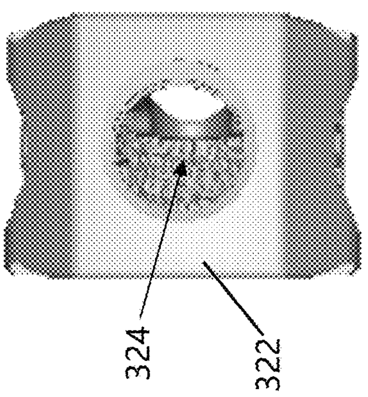
FIG. 11 is a rear plan view of the interbody implant device of another non-limiting embodiment of the present disclosure which illustrates an interbody implant device which includes a frame structure and a porous structure.
Figure 12:
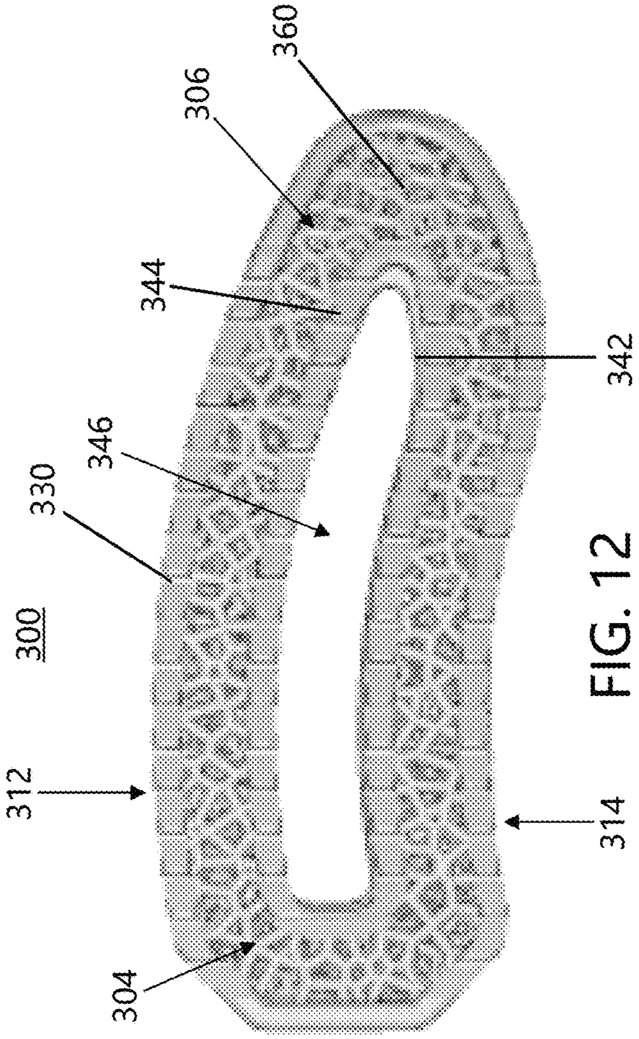
FIG. 12 bottom plan view of the interbody implant device of FIG. 11.
Figure 13:
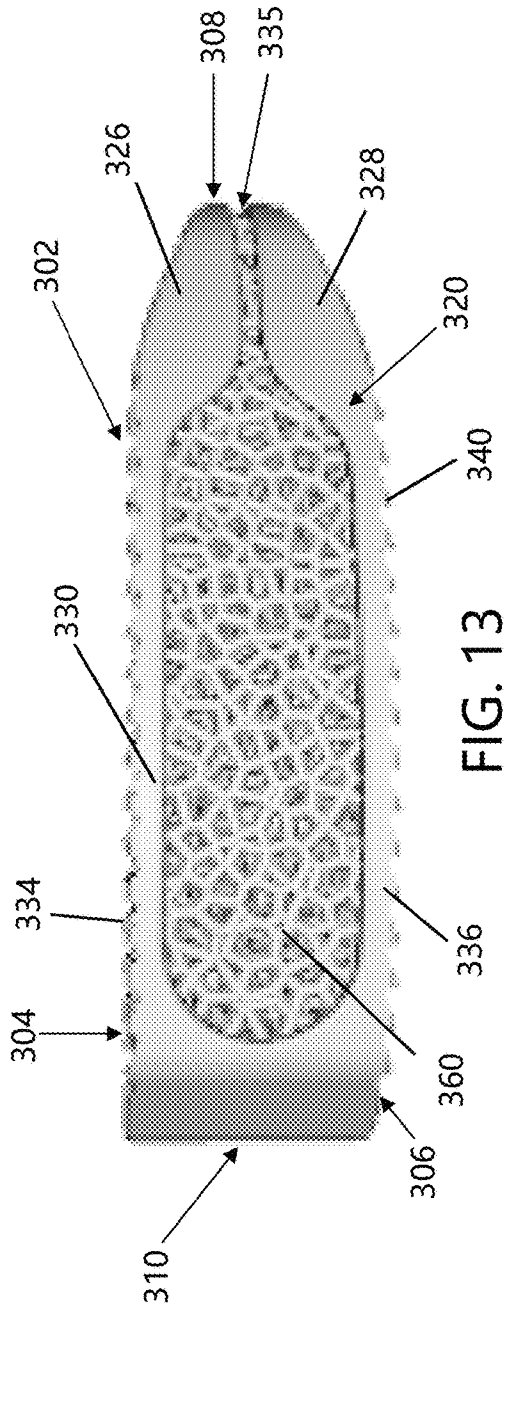
FIG. 13 is a side plan view of the interbody implant device of FIG. 11.

Referring now to FIGS. 11-13, another non-limiting interbody implant device 300 in the form of a TLIF interbody implant device is described. Many of the features of the interbody implant device 300 are the same or substantially similar to interbody implant device 100 as discussed above, thus will not be repeated herein. As illustrated in FIGS. 11-13, the shape of interbody implant device 300 is different from interbody implant device 100. The different shape allows interbody implant device 300 to be inserted in different shaped shapes between bone and/or cartilage.

The interbody implant device 300 is specially adapted for use between bony structures and generally includes at least six unique surfaces which define a body or 3D profile 302 of the interbody implant device 300. An external frame structure 320 and integral internal porous structure 360 structurally support the interbody implant device 300 such that the general shape of the 3D profile 302 and overall structural integrity can be maintained during the lifespan of the interbody implant device 300. The porous structure 360 is generally positioned at least partially within the frame structure. Furthermore, the porous structure 360 can optionally be configured to extend to and to form at least a portion of each surface which defines the 3D profile 302.

The six unique surfaces which define the 3D profile 302 of the interbody implant device 300 include, but are not limited to, top and bottom surfaces 304, 306, front and rear walls 308, 310, and first and second sidewalls 312, 314 extending between the front and rear walls. The walls 308-314 are generally configured to place the top and bottom surfaces 304, 306 in spaced apart relation. In various non-limiting embodiments discussed herein, the top and bottom surfaces may generally be oriented along converging planes, diverging planes, and/or parallel planes.

The top and bottom surfaces 304, 306 extend from the rear wall 310 to the front wall 308 along both converging and diverging planes. As best illustrated in FIG. 13, the top and bottom surfaces 304, 306 moving from the rear wall 310 to the front wall 308 initially are generally parallel to one another about 30-95% (and all values and ranges therebetween) of the longitudinal length of the interbody implant device 300, and typically the rear wall 310 to the front wall 308 are generally parallel to one another about 55-90% of the longitudinal length of the interbody implant device 300. Thereafter, the top and bottom surfaces 304, 306 lie in converging planes. In other words, top and bottom surfaces 304, 306 are spaced apart a greatest distance at the location where the top and bottom surfaces 304, 306 are generally parallel to one another. However, as mentioned above, such a configuration is non-limiting.

As also illustrated in FIG. 12, the side walls have an arcuate or curved outer surface profile. As such the central longitudinal axis of the interbody implant device 300 is arcuate or curved. The first side wall 312 initially has an upward curved slope and then a downward curved slope. The second side wall 314 initially has an upward curved slope and then a downward curved slope and then again has an upward curved slope. The corresponding inner wall formed between inner top rim 342 and the inner bottom rim 344 has a generally corresponding shape to the respective first and second side walls 312, 314.

In addition, the profile 302 of the interbody implant device 300 may include an optional smooth lead-in portion or optional taper located adjacent the front wall 308 and formed by at least a portion of both top and bottom surfaces 304, 306. The taper (when used) is configured to aid in the insertion of the interbody implant device 300 between the bone and/or cartilage.

The frame structure 320 illustrated in FIGS. 11-13 will now be described in further detail. In some particular non-limiting embodiments, the frame structure 320 is generally defined by a rear plate 322 spaced apart from top and bottom front plates 326, 328, outer top and bottom rims 330, 336, and inner top and bottom rims 342, 344. The top rim 330 is connected to the top of the rear plate 322 and to the top of front plate 326. The bottom rim 336 is connected to the bottom of the rear plate 322 and to the bottom of bottom plate 328.

As seen in FIG. 11, an aperture 324 optionally formed in the rear plate 322 provides a screw opening configured to provide a rigid connection with a tool or instrument used for inserting the implant device 300. The plate elements 322, 326, 328 and the rim elements 330, 336, 342, 344 are all generally connected to the porous structure 360, which is positioned at least partially within the frame structure 320. The outer top and bottom rims 330, 336 are spaced apart from one another and are each configured to provide at least one point of connection with the plate members 322, 326, and 328.

As illustrated in FIG. 11, the rear plate 322 extends fully between and connects to both the outer top rim 330 and outer bottom rim 336 on the rear wall 310. As illustrated in FIG. 11, the rear plate 322 forms substantially (80-100% and all values and ranges therebetween) the full the rear portion of the interbody implant device 300. As illustrated in FIG. 13, the rear wall 310 can optionally extend to a portion of one or both sides of the interbody implant device 300. As illustrated in FIG. 13, the rear wall 310 covers about 0-25% (and all values and ranges therebetween) of one or both sides of the interbody implant device 300, and typically the rear wall 310 covers about 1-10% of one or both sides of the interbody implant device 300.

As illustrated in FIG. 13, the top front plate 326 connects to the outer top rim 330 and the bottom front plate 328 connects to the outer bottom rim 336 on the front wall 308. The top and bottom front plates 326, 328 are also spaced from one another to form a front plate gap 335 on the front wall 308. The front plate gap 335 advantageously allows for the load applied to the porous structure 360, thereby reducing the stiffness of the body profile 302 of the interbody implant device 300. The top front plate 326 and bottom front plate 328 generally covers 15-98% (and all values and ranges therebetween) of the front surface of the interbody implant device 300, and typically covers 51-95% of the front surface of the interbody implant device 300. The top and/or bottom front plates 330, 336 can optionally form a portion of one or both sides of the interbody implant device 300. In one specific non-limiting arrangement, the top and/or bottom front plates 330, 336 can optionally form 0-60% (and all values and ranges therebetween) of one or both sides of the interbody implant device 300, and typically the top and/or bottom front plates 330, 336 can optionally form 1-45% of one or both sides of the interbody implant device 300.

The outer top rim 330 forms an outer peripheral edge of the top surface 304 and the outer bottom rim 336 forms an outer peripheral edge of the bottom surface 306. Generally, the outer top rim 330 and the outer bottom rim 336 are formed of smooth surfaces to reduce or eliminate any sharp outer peripheral surfaces on the outer top rim 330 and/or the outer bottom rim 336; however, this is not required.

As illustrated in FIG. 13, the top front plate 326 forms at least part of an upper portion of the front wall 308 and the bottom front plate 328 forms at least part of a lower portion of the front wall. The front plate gap 335 generally is located ±0-10% (and all values and ranges therebetween) of the central longitudinal axis or plane of the interbody implant device 300, and typically the front plate gap 335 generally is located ±0-5% of the central longitudinal axis or plane of the interbody implant device 300. The outer top rim 330 and/or the outer bottom rim 336 can optionally form a portion of the back surface of the interbody implant device 300. Generally, the outer top rim 330 and/or the outer bottom rim 336 forms 0-30% (and all values and ranges therebetween) of the back surface of the interbody implant device 300, and typically the outer top rim 330 and/or the outer bottom rim 336 forms 0-15% of the back surface of the interbody implant device 300. The outer top rim 330 and/or the outer bottom rim 336 can optionally form a portion of the front surface of the interbody implant device 300. Generally, the outer top rim 330 and/or the outer bottom rim 336 forms 0-20% (and all values and ranges therebetween) of the front surface of the interbody implant device 300, and typically the outer top rim 330 and/or the outer bottom rim 336 forms 0-10% of the front surface of the interbody implant device 300. The outer top rim 330 and/or the outer bottom rim 336 typically forms a portion of the one or both side surfaces of the interbody implant device 300. Generally, the outer top rim 330 and/or the outer bottom rim 336 forms 1-60% (and all values and ranges therebetween) of one or both side surfaces of the interbody implant device 300, and typically the outer top rim 330 and/or the outer bottom rim 336 forms 2-40% of one or both side surfaces one or both side surfaces of the interbody implant device 300.

In some non-limiting embodiments, one or more surface serrations or teeth 334 are formed on the outer top rim 330. In addition or alternatively, the outer bottom rim 336 can have one or more surface serrations or teeth 340 formed thereon. The one or more surface serrations or teeth 334, 340 (best seen in FIG. 13) are generally configured to help prevent the interbody implant device 300 from backing out after the device has been inserted. However, such a configuration is non-limiting.

The inner top and bottom rims 342, 344 are spaced apart from one another. Moreover, the inner top and bottom rims 342, 344 are spaced apart from the outer top and bottom rims 330, 336, respectively. In some particular non-limiting embodiments, the inner top and bottom rims 342/344 are spaced in a concentric manner to the outer top and bottom rims 330, 336, respectively. The thickness of the inner top rim 342 is about 1-40% (and all values and ranges therebetween) the maximum width between the inner top rim 342 and the outer top rim 330, and typically the thickness of the inner top rim 342 is about 2-15% the maximum width between the inner top rim 342 and the outer top rim 330. The thickness of the outer top rim 330 is about 1-40% (and all values and ranges therebetween) the maximum width between the inner top rim 342 and the outer top rim 330, and typically the thickness of the outer top rim 330 is about 2-15% the maximum width between the inner top rim 342 and the outer top rim 330. The thickness of the inner bottom rim 344 is about 1-40% (and all values and ranges therebetween) the maximum width between the inner bottom rim 344 and the outer bottom rim 336, and typically the thickness of the inner bottom rim 344 is about 2-15% the maximum width between the inner bottom rim 344 and the outer bottom rim 336. The thickness of the outer bottom rim 336 is about 1-40% (and all values and ranges therebetween) the maximum width between the inner bottom rim 344 and the outer bottom rim 336, and typically the thickness of the outer bottom rim 336 is about 2-15% the maximum width between the inner bottom rim 344 and the outer bottom rim 336.

As best seen in FIG. 13, the outer top and bottom rims 330, 336 are spaced apart from one another. The width/height of the outer top rim 330 is about 1-40% (and all values and ranges therebetween) the maximum width/height between the outer top rim 330 and the outer bottom top rim 336, and typically the width/height of the outer top rim 330 is about 2-15% the maximum width/height between the outer top rim 330 and the outer bottom top rim 336. The width/height of the outer bottom rim 336 is about 1-40% (and all values and ranges therebetween) the maximum width/height between the outer top rim 330 and the outer bottom top rim 336, and typically the width/height of the outer bottom rim 336 is about 2-15% the maximum width/height between the outer top rim 330 and the outer bottom top rim 336.

With continued reference to FIG. 12, the frame structure 320 further includes a central opening 346 defined within an inner perimeter of the body profile 302. The central opening 346 has an upper perimeter defined by the inner top rim 342 and a lower perimeter defined by the inner bottom rim 344. The central opening 346 is generally configured to receive one or more materials including, but not limited to, bone growth-promoting materials, drugs, and cartilage, for example. Generally, the cross-sectional size of the central opening 346 is at least 10% of the cross-sectional size of the interbody implant device 300. As illustrated in FIG. 12, the size of the cross-sectional size of the central opening 346 at the bottom surface 306 is about 5-80% (and all values and ranges therebetween) of the cross-sectional size of the bottom surface 306 of interbody implant device 300, and typically the size of the cross-sectional size of the central opening 346 at the bottom surface 306 is about 10-70% of the cross-sectional size of the bottom surface of interbody implant device 300. The size of the cross-sectional size of the central opening 346 at the top surface 304 is about 5-80% (and all values and ranges therebetween) of the cross-sectional size of the top surface 304 of interbody implant device 300, and typically the size of the cross-sectional size of the central opening 346 at the top surface 304 is about 10-70% of the cross-sectional size of the top surface 304 of interbody implant device 300.

As best seen in FIG. 12, a bottom surface of the inner top rim 342 and a top surface of the inner bottom rim 344 are optionally partially or fully absent the porous material which forms the porous structure 360. In this regard, an upper undercut is optionally formed in the central opening 346 at the bottom surface of inner top rim 342 due to the at least partial void of porous material. Similarly, a lower undercut is also optionally formed in the central opening 346 at the top surface of inner bottom rim 344 due to the at least partial void of porous material. The upper and lower undercuts (when formed) thus increase the amount of material which can be packed into the central opening 346. In one non-limiting embodiment, the width of the upper undercut, when formed, is 5-99.5% (and all values and ranges therebetween) the width of the inner top rim 342. In one non-limiting embodiment, the width of the lower undercut (when formed) is 5-99.5% (and all values and ranges therebetween) the width of the inner bottom rim 344. In some embodiments, the upper/lower undercut extends inward relative to the central opening 346 a distance of from about 0.05-15 mm (and all values and ranges therebetween).

In some non-limiting embodiments, the frame structure 320 is formed to provide outer surfaces having an Ra roughness profile, or arithmetic mean roughness. In some particular non-limiting embodiments, the outer surfaces of frame structure 320 has a roughness Ra of from about 0.01 micron to about 3 micron (and all values and ranges therebetween). In some embodiments, the frame structure 320 has a resulting contact angle of from about 5-60° (and all values and ranges therebetween).

A metallic coating is optionally applied to one or both of the frame structure 320 and porous structure 360. The metallic coating has a thickness of from about 0.000001-0.1 in. (and all values and ranges therebetween).

The frame structure 320 typically does not include or utilize support struts within the 3D profile 302 of the interbody implant device. Specifically, no support struts are connected between the outer top and bottom rims 330/336, the rear plate 322 and the top and bottom front plates 326/328, and the inner top rim 342 and the inner bottom rim 344.

The porous material of the porous structure 360 extends to and forms at least a portion of each surface 304, 306, 308, 310, 312, and 314. The porous structure 360 includes a plurality of voids or open pores and a plurality of webs which together form a pattern or lattice. In accordance with some non-limiting embodiments, the porous structure 360 is a 3D printed structure made using any suitable additive manufacturing technique known in the art. In some other non-limiting embodiments, the porous material forming the porous structure 360 has an average density that is less than an average density of the body profile 302, the rear plate 322, the top front plate 326, the bottom front plate 328, the outer top rim 330, and/or the outer bottom rim 336.

Interbody implant device 300 is an example of a TLIF interbody. The interbody implant device 300 can be formed of titanium alloy; however, other materials can be used. The lattice structure has dimensions of 24 mm, 28 mm, and 32 mm; however, other lengths can be used. The heights can be 8-14 mm (and all values and ranges therebetween); however, other heights can be used. The lordosis can be 7° or 11° (and all values and ranges therebetween); however, other lordosis can be used.

Figure 15:
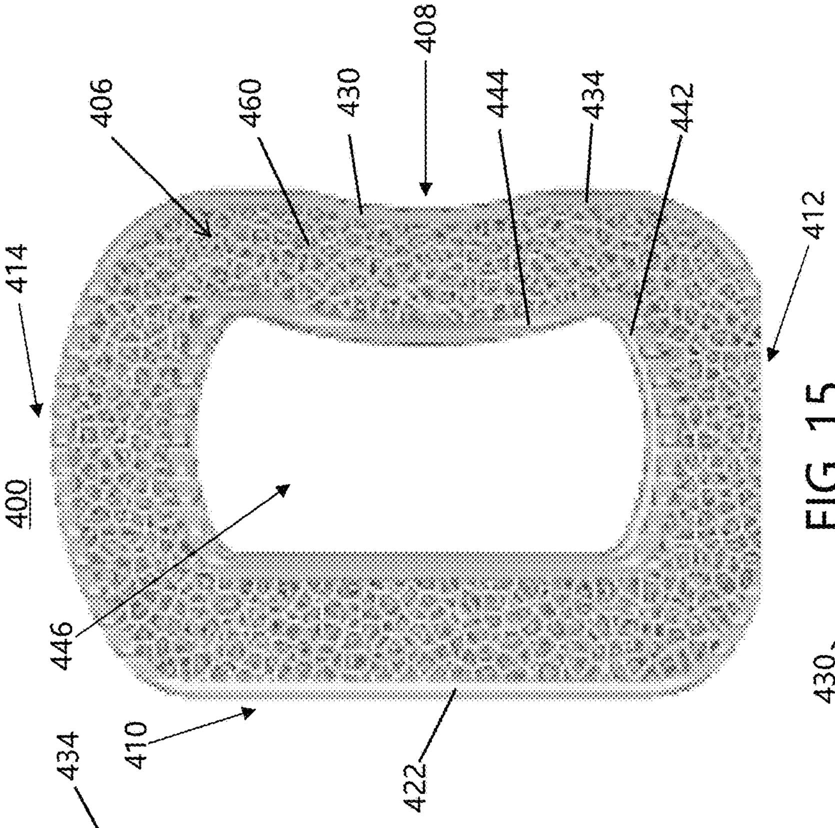
FIG. 15 bottom plan view of the interbody implant device of FIG. 14.
Figure 16:
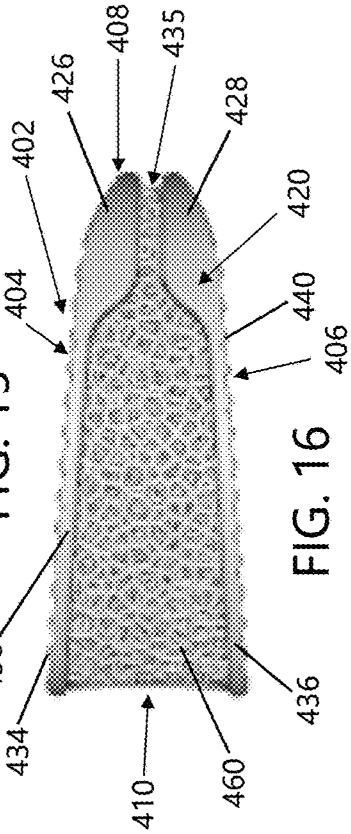
FIG. 16 is a side plan view of the interbody implant device of FIG. 14.
Figure 14:
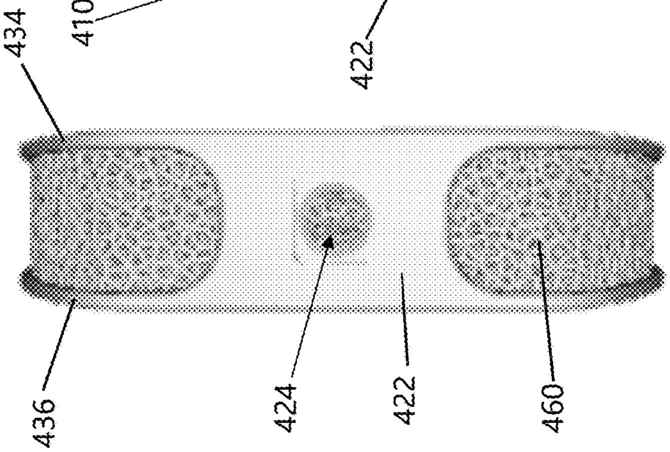
FIG. 14 is a rear plan view of the interbody implant device of another non-limiting embodiment of the present disclosure which illustrates an interbody implant device which includes a frame structure and a porous structure.

Referring now to FIGS. 14-16, another non-limiting interbody implant device 400 in the form of an ALIF interbody implant device is described. Many of the features of the interbody implant device 400 are the same or substantially similar to interbody implant device 100 as discussed above, thus will not be repeated herein. As illustrated in FIGS. 14-16, the shape of interbody implant device 400 is different from interbody implant device 100. The different shape allows interbody implant device 400 to be inserted in different shaped shapes between bone and/or cartilage.

The interbody implant device 400 is specially adapted for use between bony structures and generally includes at least six unique surfaces which define a body or 3D profile 402 of the interbody implant device 400. An external frame structure 420 and integral internal porous structure 460 structurally support the interbody implant device 400 such that the general shape of the 3D profile 402 and overall structural integrity can be maintained during the lifespan of the interbody implant device 400. The porous structure 460 is generally positioned at least partially within the frame structure. Furthermore, the porous structure 460 can optionally be configured to extend to and to form at least a portion of each surface which defines the 3D profile 402.

The six unique surfaces which define the 3D profile 402 of the interbody implant device 400 include, but are not limited to, top and bottom surfaces 404, 406, front and rear walls 408, 410, and first and second sidewalls 412, 414 extending between the front and rear walls. The walls 408-414 are generally configured to place the top and bottom surfaces 404, 406 in spaced apart relation. In various non-limiting embodiments discussed herein, the top and bottom surfaces may generally be oriented along converging planes, diverging planes, and/or parallel planes.

The top and bottom surfaces 404/406 extend from the rear wall 410 to the front wall 408 along both converging and diverging planes. As best illustrated in FIG. 16, the top and bottom surfaces 404, 406 moving from the rear wall 410 to the front wall 408 are in converging planes along about 30-95% (and all values and ranges therebetween) of the longitudinal length of the interbody implant device 400. In other words, top and bottom surfaces 404, 406 are spaced apart a greatest distance at the rear wall 410 and a shortest distance at the front wall 408. However, as mentioned above, such a configuration is non-limiting.

As illustrated in FIG. 15, the second side wall 414 has a generally curved outer surface profile, and the first side wall 412 has a generally straight or planar profile. As such, the first side wall 412 and second side wall 414 are not parallel to one another along the respective lengths of the side walls. The corresponding inner wall formed between inner top rim 442 and the inner bottom rim 444 has a generally corresponding shape to the respective first and second side walls 412, 414. The rear wall 410 has a generally straight or planar profile along over 50% the length of the rear wall. The front wall 408 has a generally curved profile. As illustrated in FIG. 15, the front wall 408 initially curves generally downwardly and then curves upwardly along the length of the front wall.

In addition, the profile 402 of the interbody implant device 400 may include an optional smooth lead-in portion or optional taper located adjacent the front wall 408 and formed by at least a portion of both top and bottom surfaces 404/406. The taper (when used) is configured to aid in the insertion of the interbody implant device 400 between the bone and/or cartilage.

The frame structure 420 illustrated in FIGS. 14-16 will now be described in further detail. In some non-limiting embodiments, the frame structure 420 is generally defined by a rear plate 422 spaced apart from top and bottom front plates 426, 428, outer top and bottom rims 430, 436, and inner top and bottom rims 442, 444. The top rim 430 is connected to the top of the rear plate 422 and to the top of front plate 426. The bottom rim 436 is connected to the bottom of the rear plate 422 and to the bottom of bottom plate 428.

As seen in FIG. 14, an aperture 424 optionally formed in the rear plate 422 provides a screw opening configured to provide a rigid connection with a tool or instrument used for inserting the implant device 400. The plate elements 422, 426, 428 and the rim elements 430, 436, 442, 444 are all generally connected to the porous structure 460, which is positioned at least partially within the frame structure 420. The outer top and bottom rims 430, 436 are spaced apart from one another and are each configured to provide at least one point of connection with the plate members 422, 426, and 428.

As illustrated in FIG. 14, the rear plate 422 extends fully between and connects to both the outer top rim 430 and outer bottom rim 436 on the rear wall 410. As illustrated in FIG. 14, the rear plate 422 forms 10-100% (and all values and ranges therebetween) the rear portion of the interbody implant device 400. The rear wall 410 can optionally extend to a portion of one or both sides of the interbody implant device 400. As illustrated in FIG. 14, the rear wall 410 covers about 0-25% (and all values and ranges therebetween) of one or both sides of the interbody implant device 400.

As illustrated in FIG. 16, the top front plate 426 connects to the outer top rim 430 and the bottom front plate 428 connects to the outer bottom rim 436 on the front wall 408. The top and bottom front plates 426, 428 are also spaced from one another to form a front plate gap 435 on the front wall 408. The front plate gap 435 advantageously allows for the load applied to the porous structure 460, thereby reducing the stiffness of the body profile 402 of the interbody implant device 400. The top front plate 426 and bottom front plate 428 generally covers 15-98% (and all values and ranges therebetween) of the front surface of the interbody implant device 400, and typically covers 51-95% of the front surface of the interbody implant device 400. The top and/or bottom front plates 430, 436 can optionally form a portion of one or both sides of the interbody implant device 400. In one specific non-limiting arrangement, the top and/or bottom front plates 430, 436 can optionally form 0-60% (and all values and ranges therebetween) of one or both sides of the interbody implant device 400, and typically the top and/or bottom front plates 430, 436 can optionally form 1-45% of one or both sides of the interbody implant device 400.

The outer top rim 430 forms an outer peripheral edge of the top surface 404 and the outer bottom rim 436 forms an outer peripheral edge of the bottom surface 406. Generally, the outer top rim 430 and the outer bottom rim 436 are formed of smooth surfaces to reduce or eliminate any sharp outer peripheral surfaces on the outer top rim 430 and/or the outer bottom rim 436; however, this is not required.

As illustrated in FIG. 16, the top front plate 426 forms at least part of an upper portion of the front wall 408 and the bottom front plate 428 forms at least part of a lower portion of the front wall. The front plate gap 435 generally is located ±0-10% (and all values and ranges therebetween) of the central longitudinal axis or plane of the interbody implant device 400, and typically the front plate gap 435 generally is located ±0-5% of the central longitudinal axis or plane of the interbody implant device 400. The outer top rim 430 and/or the outer bottom rim 436 can optionally form a portion of the back surface of the interbody implant device 400. Generally, the outer top rim 430 and/or the outer bottom rim 436 forms 0-30% (and all values and ranges therebetween) of the back surface of the interbody implant device 400, and typically the outer top rim 430 and/or the outer bottom rim 436 forms 0-15% of the back surface of the interbody implant device 400. The outer top rim 430 and/or the outer bottom rim 436 can optionally form a portion of the front surface of the interbody implant device 400. Generally, the outer top rim 430 and/or the outer bottom rim 436 forms 0-20% (and all values and ranges therebetween) of the front surface of the orthopedic implant device 400, and typically the outer top rim 430 and/or the outer bottom rim 436 forms 0-10% of the front surface of the interbody implant device 400. The outer top rim 430 and/or the outer bottom rim 436 typically forms a portion of the one or both side surfaces of the interbody implant device 400. Generally, the outer top rim 430 and/or the outer bottom rim 436 forms 1-60% (and all values and ranges therebetween) of one or both side surfaces of the interbody implant device 400, and typically the outer top rim 430 and/or the outer bottom rim 436 forms 2-40% of one or both side surfaces one or both side surfaces of the interbody implant device 400.

In some non-limiting embodiments, one or more surface serrations or teeth 434 are formed on the outer top rim 430. In addition or alternatively, the outer bottom rim 436 can have one or more surface serrations or teeth 440 formed thereon. The one or more surface serrations or teeth 434/440 (best seen in FIG. 16) are generally configured to help prevent the interbody implant device 400 from backing out after the device has been inserted. However, such a configuration is non-limiting.

The inner top and bottom rims 442, 444 are spaced apart from one another. Moreover, the inner top and bottom rims 442, 444 are spaced apart from the outer top and bottom rims 430, 436, respectively. In some particular non-limiting embodiments, the inner top and bottom rims 442/444 are spaced in a concentric manner to the outer top and bottom rims 430, 436, respectively. The thickness of the inner top rim 442 is about 1-40% (and all values and ranges therebetween) the maximum width between the inner top rim 442 and the outer top rim 430, and typically the thickness of the inner top rim 442 is about 2-15% the maximum width between the inner top rim 442 and the outer top rim 430. The thickness of the outer top rim 430 is about 1-40% (and all values and ranges therebetween) the maximum width between the inner top rim 442 and the outer top rim 430, and typically the thickness of the outer top rim 430 is about 2-15% the maximum width between the inner top rim 442 and the outer top rim 430. The thickness of the inner bottom rim 444 is about 1-40% (and all values and ranges therebetween) the maximum width between the inner bottom rim 444 and the outer bottom rim 436, and typically the thickness of the inner bottom rim 444 is about 2-15% the maximum width between the inner bottom rim 444 and the outer bottom rim 436. The thickness of the outer bottom rim 436 is about 1-40% (and all values and ranges therebetween) the maximum width between the inner bottom rim 444 and the outer bottom rim 436, and typically the thickness of the outer bottom rim 436 is about 2-15% the maximum width between the inner bottom rim 444 and the outer bottom rim 436.

As best seen in FIG. 16, the outer top and bottom rims 430, 436 are spaced apart from one another. The width/height of the outer top rim 430 is about 1-40% (and all values and ranges therebetween) the maximum width/height between the outer top rim 430 and the outer bottom top rim 436, and typically the width/height of the outer top rim 430 is about 2-15% the maximum width/height between the outer top rim 430 and the outer bottom top rim 436. The width/height of the outer bottom rim 436 is about 1-40% (and all values and ranges therebetween) the maximum width/height between the outer top rim 430 and the outer bottom top rim 436, and typically the width/height of the outer bottom rim 436 is about 2-15% the maximum width/height between the outer top rim 430 and the outer bottom top rim 436.

With continued reference to FIG. 15, the frame structure 420 further includes a central opening 446 defined within an inner perimeter of the body profile 402. The central opening 446 has an upper perimeter defined by the inner top rim 442 and a lower perimeter defined by the inner bottom rim 444. The central opening 446 is generally configured to receive one or more materials including, but not limited to, bone growth-promoting materials, drugs, and cartilage, for example. Generally, the cross-sectional size of the central opening 446 is at least 10% of the cross-sectional size of the interbody implant device 400. As illustrated in FIG. 15, the size of the cross-sectional size of the central opening 446 at the bottom surface 406 is about 5-80% (and all values and ranges therebetween) of the cross-sectional size of the bottom surface 406 of interbody implant device 400, and typically the size of the cross-sectional size of the central opening 446 at the bottom surface 406 is about 10-70% of the cross-sectional size of the bottom surface 406 of interbody implant device 400. The size of the cross-sectional size of the central opening 446 at the top surface 404 is about 5-80% (and all values and ranges therebetween) of the cross-sectional size of the top surface 404 of interbody implant device 400, and typically the size of the cross-sectional size of the central opening 446 at the top surface 404 is about 10-70% of the cross-sectional size of the top surface 404 of interbody implant device 400.

As best seen in FIG. 15, a bottom surface of the inner top rim 442 and a top surface of the inner bottom rim 444 are optionally partially or fully absent the porous material which forms the porous structure 460. In this regard, an upper undercut is optionally formed in the central opening 446 at the bottom surface of inner top rim 442 due to the at least partial void of porous material. Similarly, a lower undercut is also optionally formed in the central opening 446 at the top surface of inner bottom rim 444 due to the at least partial void of porous material. The upper and lower undercuts (when formed) thus increase the amount of material which can be packed into the central opening 446. In one non-limiting embodiment, the width of the upper undercut (when formed) is 5-99.5% (and all values and ranges therebetween) the width of the inner top rim 442. In one non-limiting embodiment, the width of the lower undercut (when formed) is 5-99.5% (and all values and ranges therebetween) the width of the inner bottom rim 444. In some embodiments, the upper/lower undercut extends inward relative to the central opening 446 a distance of from about 0.05-15 mm (and all values and ranges therebetween).

In some non-limiting embodiments, the frame structure 420 is formed to provide outer surfaces having an Ra roughness profile or arithmetic mean roughness. In some embodiments, the outer surfaces of frame structure 420 has a roughness Ra of from about 0.01-3 microns (and all values and ranges therebetween). In some embodiments, the frame structure 420 has a resulting contact angle of from about 5-60° (and all values and ranges therebetween).

A metallic coating is optionally applied to one or both of the frame structure 420 and porous structure 460. The metallic coating has a thickness of from about 0.000001-0.1 inches (and all values and ranges therebetween).

The frame structure 420 typically does not include or utilize support struts within the 3D profile 402 of the interbody implant device. Specifically, no support struts are connected between the outer top and bottom rims 430, 436, the rear plate 422 and the top and bottom front plates 426, 428, and the inner top rim 442 and the inner bottom rim 444.

The porous material of the porous structure 460 extends to and forms at least a portion of each surface 404, 406, 408, 410, 412, and 414. The porous structure 460 includes a plurality of voids or open pores and a plurality of webs which together form a pattern or lattice. In accordance with some non-limiting embodiments, the porous structure 460 is a 3D printed structure made using any suitable additive manufacturing technique known in the art. In some other non-limiting embodiments, the porous material forming the porous structure 460 has an average density that is less than an average density of the body profile 402, the rear plate 422, the top front plate 426, the bottom front plate 428, the outer top rim 430, and/or the outer bottom rim 436.

Interbody implant device 400 is an example of an ALIF interbody. The interbody implant device 400 can be formed of titanium alloy; however, other materials can be used. The lattice structure has dimensions of 24 mm×34 mm, or 30 mm×40 mm; however, other lengths can be used. The heights can be 8-20 mm (and all values and ranges therebetween); however, other heights can be used. The lordosis can be 8° or 14° (and all values and ranges therebetween); however, other lordosis can be used.

Figures 17, 18:
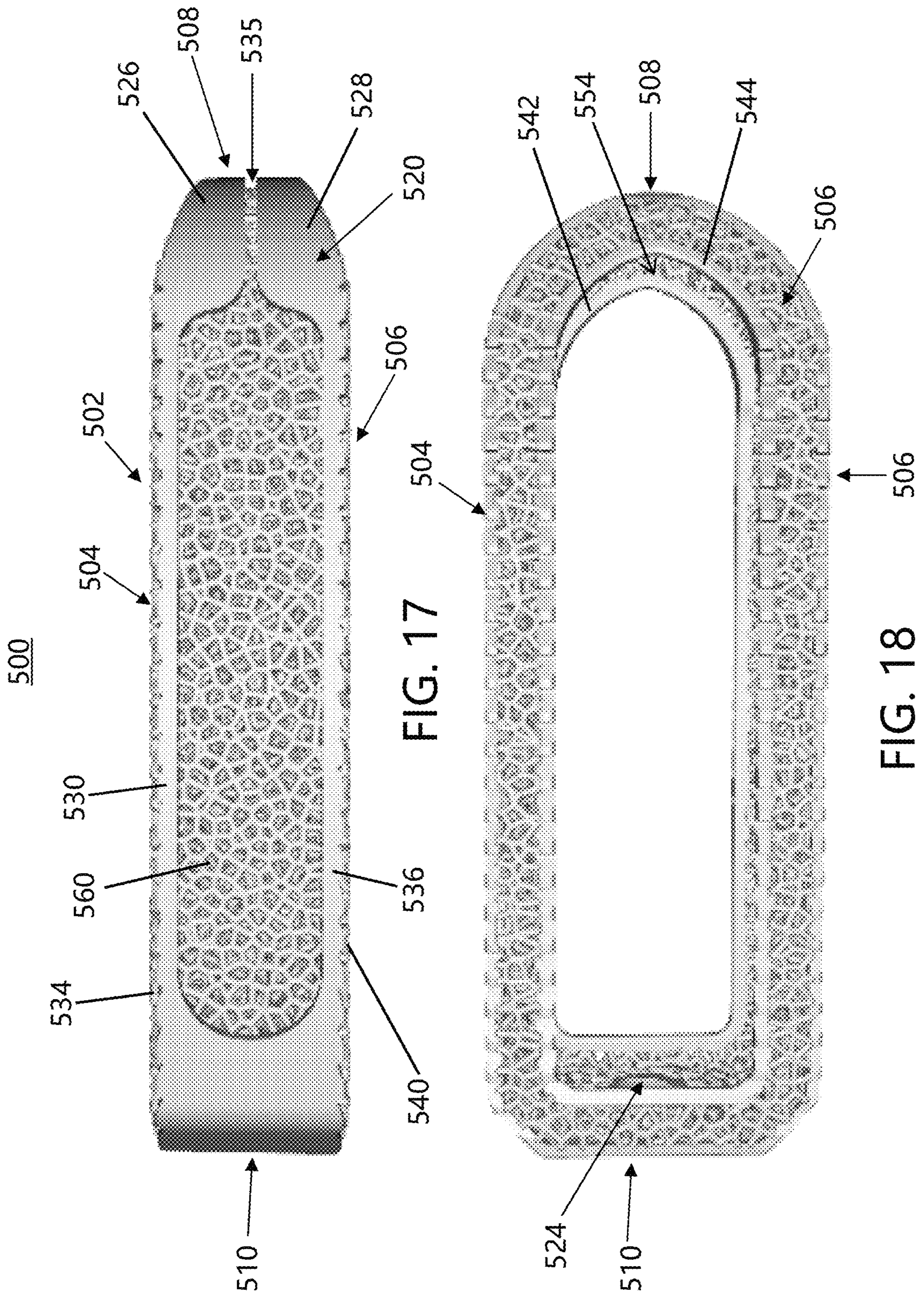
FIG. 17 is a side plan view of the interbody implant device of another non-limiting embodiment of the present disclosure which illustrates an interbody implant device which includes a frame structure and a porous structure; and, FIG. 18 bottom plan view of the interbody implant device of FIG. 17.

Referring now to FIGS. 17-18, another non-limiting interbody implant device 500 in the form of an LLIF interbody implant device is described. Many of the features of the interbody implant device 500 are the same or substantially similar to interbody implant device 100 as discussed above, thus will not be repeated herein. As illustrated in FIGS. 17-18, the shape of interbody implant device 500 is different from interbody implant device 100. The different shape allows interbody implant device 500 to be inserted in different shaped shapes between bone and/or cartilage.

The interbody implant device 500 is specially adapted for use between bony structures and generally includes at least six unique surfaces which define a body or 3D profile 502 of the interbody implant device 500. An external frame structure 520 and integral internal porous structure 560 structurally support the interbody implant device 500 such that the general shape of the 3D profile 502 and overall structural integrity can be maintained during the lifespan of the interbody implant device 500. The porous structure 560 is generally positioned at least partially within the frame structure. Furthermore, the porous structure 560 can optionally be configured to extend to and to form at least a portion of each surface which defines the 3D profile 502.

The six unique surfaces which define the 3D profile 502 of the interbody implant device 500 include, but are not limited to, top and bottom surfaces 504, 506, front and rear walls 508, 510, and first and second sidewalls 512, 514 extending between the front and rear walls. The walls 508-514 are generally configured to place the top and bottom surfaces 504, 506 in spaced apart relation. In various non-limiting embodiments discussed herein, the top and bottom surfaces may generally be oriented along converging planes, diverging planes, and/or parallel planes.

The top and bottom surfaces 504, 506 extend from the rear wall 510 to the front wall 508 along both converging and diverging planes. As best illustrated in FIG. 17, the top and bottom surfaces 504, 506 moving from the rear wall 510 to the front wall 508 are generally parallel to one another about 60-98% (and all values and ranges therebetween) of the longitudinal length of the interbody implant device 500.

As illustrated in FIG. 18, the rear wall 510 has a generally straight or planar profile along over 50% the length of the rear wall. The front wall 508 has a generally curved profile. As illustrated in FIG. 18, the front wall 508 initially curves in a semi-circular shape along the length of the front wall.

In addition, the profile 502 of the interbody implant device 500 may include an optional smooth lead-in portion or optional taper located adjacent the front wall 508 and formed by at least a portion of both top and bottom surfaces 504, 506. The taper (when used) is configured to aid in the insertion of the interbody implant device 500 between the bone and/or cartilage.

The frame structure 520 illustrated in FIGS. 17-18 will now be described in further detail. In some particular non-limiting embodiments, the frame structure 520 is generally defined by a rear plate 522 spaced apart from top and bottom front plates 526/528, outer top and bottom rims 530/536, and inner top and bottom rims 542/544. The top rim 530 is connected to the top of the rear plate 522 and to the top of front plate 526. The bottom rim 536 is connected to the bottom of the rear plate 522 and to the bottom of bottom plate 528.

As seen in FIG. 18, an aperture 524 optionally formed in the rear plate 522 provides a screw opening configured to provide a rigid connection with a tool or instrument used for inserting the implant device 500. The plate elements 522, 526, 528 and the rim elements 530, 536, 542, 544 are all generally connected to the porous structure 560, which is positioned at least partially within the frame structure 520. The outer top and bottom rims 530, 536 are spaced apart from one another and are each configured to provide at least one point of connection with the plate members 522, 526, and 528.

As illustrated in FIG. 18, the rear plate 522 extends fully between and connects to both the outer top rim 530 and outer bottom rim 536 on the rear wall 510. As illustrated in FIG. 18, the rear plate 522 forms 10-100% (and all values and ranges therebetween) the rear portion of the interbody implant device 500. The rear wall 510 can optionally extend to a portion of one or both sides of the interbody implant device 500. As illustrated in FIG. 18, the rear wall 510 covers about 0-25% (and all values and ranges therebetween) of one or both sides of the interbody implant device 500.

As illustrated in FIG. 17, the top front plate 526 connects to the outer top rim 530 and the bottom front plate 528 connects to the outer bottom rim 536 on the front wall 508. The top and bottom front plates 526, 528 are also spaced from one another to form a front plate gap 535 on the front wall 508. The front plate gap 535 advantageously allows for the load applied to the porous structure 560, thereby reducing the stiffness of the body profile 502 of the interbody implant device 500. The top front plate 526 and bottom front plate 528 generally covers 15-98% (and all values and ranges therebetween) of the front surface of the interbody implant device 500, and typically covers 51-95% of the front surface of the interbody implant device 500. The top and/or bottom front plates 530, 536 can optionally form a portion of one or both sides of the interbody implant device 500. In one specific non-limiting arrangement, the top and/or bottom front plates 530, 536 can optionally form 0-60% (and all values and ranges therebetween) of one or both sides of the interbody implant device 500, and typically the top and/or bottom front plates 530, 536 can optionally form 1-45% of one or both sides of the interbody implant device 500.

The outer top rim 530 forms an outer peripheral edge of the top surface 504 and the outer bottom rim 536 forms an outer peripheral edge of the bottom surface 506. Generally, the outer top rim 530 and the outer bottom rim 536 are formed of smooth surfaces to reduce or eliminate any sharp outer peripheral surfaces on the outer top rim 530 and/or the outer bottom rim 536; however, this is not required.

As illustrated in FIG. 17, the top front plate 526 forms at least part of an upper portion of the front wall 508 and the bottom front plate 528 forms at least part of a lower portion of the front wall. The front plate gap 535 generally is located ±0-10% (and all values and ranges therebetween) of the central longitudinal axis or plane of the interbody implant device 500, and typically the front plate gap 535 generally is located ±0-5% of the central longitudinal axis or plane of the interbody implant device 500. The outer top rim 530 and/or the outer bottom rim 536 can optionally form a portion of the back surface of the interbody implant device 500. Generally, the outer top rim 530 and/or the outer bottom rim 536 forms 0-30% (and all values and ranges therebetween) of the back surface of the interbody implant device 500, and typically the outer top rim 530 and/or the outer bottom rim 536 forms 0-15% of the back surface of the interbody implant device 500. The outer top rim 530 and/or the outer bottom rim 536 can optionally form a portion of the front surface of the interbody implant device 500. Generally, the outer top rim 530 and/or the outer bottom rim 536 forms 0-20% (and all values and ranges therebetween) of the front surface of the interbody implant device 500, and typically the outer top rim 530 and/or the outer bottom rim 536 forms 0-10% of the front surface of the interbody implant device 500. The outer top rim 530 and/or the outer bottom rim 536 typically forms a portion of the one or both side surfaces of the interbody implant device 500. Generally, the outer top rim 530 and/or the outer bottom rim 536 forms 1-60% (and all values and ranges therebetween) of one or both side surfaces of the interbody implant device 500, and typically the outer top rim 530 and/or the outer bottom rim 536 forms 2-40% of one or both side surfaces one or both side surfaces of the interbody implant device 500.

In some non-limiting embodiments, one or more surface serrations or teeth 534 are formed on the outer top rim 530. In addition or alternatively, the outer bottom rim 536 can have one or more surface serrations or teeth 540 formed thereon. The one or more surface serrations or teeth 534, 540 (best seen in FIG. 17) are generally configured to help prevent the interbody implant device 500 from backing out after the device has been inserted. However, such a configuration is non-limiting.

The inner top and bottom rims 542, 544 are spaced apart from one another. Moreover, the inner top and bottom rims 542, 544 are spaced apart from the outer top and bottom rims 530, 536, respectively. In some particular non-limiting embodiments, the inner top and bottom rims 542, 544 are spaced in a concentric manner to the outer top and bottom rims 530, 536, respectively. The thickness of the inner top rim 542 is about 1-40% (and all values and ranges therebetween) the maximum width between the inner top rim 542 and the outer top rim 530, and typically the thickness of the inner top rim 542 is about 2-15% the maximum width between the inner top rim 542 and the outer top rim 530. The thickness of the outer top rim 530 is about 1-40% (and all values and ranges therebetween) the maximum width between the inner top rim 542 and the outer top rim 530, and typically the thickness of the outer top rim 530 is about 2-15% the maximum width between the inner top rim 542 and the outer top rim 530. The thickness of the inner bottom rim 544 is about 1-40% (and all values and ranges therebetween) the maximum width between the inner bottom rim 544 and the outer bottom rim 536, and typically the thickness of the inner bottom rim 544 is about 2-15% the maximum width between the inner bottom rim 544 and the outer bottom rim 536. The thickness of the outer bottom rim 536 is about 1-40% (and all values and ranges therebetween) the maximum width between the inner bottom rim 544 and the outer bottom rim 536, and typically the thickness of the outer bottom rim 536 is about 2-15% the maximum width between the inner bottom rim 544 and the outer bottom rim 536.

As best seen in FIG. 17, the outer top and bottom rims 530, 536 are spaced apart from one another. The width/height of the outer top rim 530 is about 1-40% (and all values and ranges therebetween) the maximum width/height between the outer top rim 530 and the outer bottom top rim 536, and typically the width/height of the outer top rim 530 is about 2-15% the maximum width/height between the outer top rim 530 and the outer bottom top rim 536. The width/height of the outer bottom rim 536 is about 1-40% (and all values and ranges therebetween) the maximum width/height between the outer top rim 530 and the outer bottom top rim 536, and typically the width/height of the outer bottom rim 536 is about 2-15% the maximum width/height between the outer top rim 530 and the outer bottom top rim 536.

With continued reference to FIG. 18, the frame structure 520 further includes a central opening 546 defined within an inner perimeter of the body profile 502. The central opening 546 has an upper perimeter defined by the inner top rim 542 and a lower perimeter defined by the inner bottom rim 544. The central opening 546 is generally configured to receive one or more materials including, but not limited to, bone growth-promoting materials, drugs, and cartilage, for example. Generally, the cross-sectional size of the central opening 546 is at least 10% of the cross-sectional size of the interbody implant device 500. As illustrated in FIG. 18, the size of the cross-sectional size of the central opening 546 at the bottom surface 506 is about 5-80% (and all values and ranges therebetween) of the cross-sectional size of the bottom surface 506 of interbody implant device 500, and typically the size of the cross-sectional size of the central opening 546 at the bottom surface 506 is about 10-70% of the cross-sectional size of the bottom surface 506 of interbody implant device 500. The size of the cross-sectional size of the central opening 546 at the top surface 504 is about 5-80% (and all values and ranges therebetween) of the cross-sectional size of the top surface 504 of interbody implant device 500, and typically the size of the cross-sectional size of the central opening 546 at the top surface 504 is about 10-70% of the cross-sectional size of the top surface 504 of interbody implant device 500.

As best seen in FIGS. 17 and 18, a bottom surface of the inner top rim 542 and a top surface of the inner bottom rim 544 are optionally partially or fully absent the porous material which forms the porous structure 560. In this regard, an upper undercut is optionally formed in the central opening 546 at the bottom surface of inner top rim 542 due to the at least partial void of porous material. Similarly, a lower undercut is also optionally formed in the central opening 546 at the top surface of inner bottom rim 544 due to the at least partial void of porous material. The upper and lower undercuts, when formed, thus increase the amount of material which can be packed into the central opening 546. In one non-limiting embodiment, the width of the upper undercut, when formed, is 5-99.5% (and all values and ranges therebetween) the width of the inner top rim 542. In one non-limiting embodiment, the width of the lower undercut, when formed, is 5-99.5% (and all values and ranges therebetween) the width of the inner bottom rim 544. In some particular non-limiting embodiments, the upper/lower undercut extends inward relative to the central opening 546 a distance of from about 0.05 mm to about 15 mm (and all values and ranges therebetween).

In some non-limiting embodiments, the frame structure 520 is formed to provide outer surfaces having an Ra roughness profile or arithmetic mean roughness. In some embodiments, the outer surfaces of frame structure 520 has a roughness Ra of from about 0.01-3 micron (and all values and ranges therebetween). In some embodiments, the frame structure 520 has a resulting contact angle of from about 5-60° (and all values and ranges therebetween).

A metallic coating is optionally applied to one or both of the frame structure 520 and porous structure 560. The metallic coating has a thickness of from about 0.000001-0.1 inches (and all values and ranges therebetween).

The frame structure 520 typically does not include or utilize support struts within the 3D profile 502 of the interbody implant device. Specifically, no support struts are connected between the outer top and bottom rims 530, 536, the rear plate 522 and the top and bottom front plates 526, 528, and the inner top rim 542 and the inner bottom rim 544.

The porous material of the porous structure 560 extends to and forms at least a portion of each surface 504, 506, 508, 510, 512, and 514. The porous structure 560 includes a plurality of voids or open pores and a plurality of webs which together form a pattern or lattice. In accordance with some non-limiting embodiments, the porous structure 560 is a 3D printed structure made using any suitable additive manufacturing technique known in the art. In some other non-limiting embodiments, the porous material forming the porous structure 560 has an average density that is less than an average density of the body profile 502, the rear plate 522, the top front plate 526, the bottom front plate 528, the outer top rim 530, and/or the outer bottom rim 536.

Interbody implant device 500 is an example of an LLIF interbody. The interbody implant device 500 can be formed of titanium alloy; however, other materials can be used. The lattice structure has dimensions of 40-55 mm length, 18 mm width and 22 mm width, and 8-16 mm height; however, other lengths, widths, and heights can be used. The lordosis can be 0° or 8° (and all values and ranges therebetween); however, other lordosis can be used.

Moreover, various process parameters are used to form the 3D printed porous structure 160, 260, 360, 460, 560 such that the plurality of pores 162 and webs 164 are not arranged in any particular order and the pattern 166 is completely randomized. Use of a randomized pattern of pores and webs is advantageous for mimicking the structure cancellous bone.

Exemplary process parameters which may be entered into an associated software suite specially configured to generate code for instructing an associated 3D printer on how to print a desired structure are provided in Tables 1 and 2. Table 1 provides exemplary process parameters which may be used to generate a randomized pattern (such as randomized pattern 166) for a base lattice out of a solid or surface body. Table 2 provides exemplary process parameters which may be used to add a surface roughness lattice to the base lattice generated as a result of the process parameters from Table 1. A rough lattice structure is advantageous because it allows for initial stabilization when the lattice structure contacts the plate components of the frame structure 120, 220, 320, 420, 520.

The names of specific process parameters are listed in the first columns of Tables 1 and 2 below. The remaining columns provide a nominal, minimum, and maximum value for each of the parameters from column 1. As can be appreciated, all of the values between the minimum and maximum values can be used. The nominal values are predetermined based on the specific spinal disc and/or vertebral body to be replaced by the interbody implant device 100, 200, 300, 400, 500. The minimum and maximum values represent an allowable range from which specific values can be chosen for each process parameter to form additional stochastic or randomized lattices which may be suitable for use as the porous structure in the implant devices disclosed herein.

TABLE 1

| Process Parameters for Forming Stochastic Lattice Base Lattice | | | |
|---|---|---|---|
| Stochastic Lattice | Nominal | Min | Max |
| Rule | Voronoi (Volume) | NA | NA |
| Target Cell diameter (mm) | 0.8 | 0.05 | 3 |
| Random Seed | 0.4 | 0.01 | 1 |
| Diameter (mm) | 0.4 | 0.1 | 2 |
| Mesh | | | |
| Mesh Resolution | 0 | 0 | 1 |
| Node Smoothing | 0 | 0 | 1 |
| Mesh Cleanup | Yes | No | Yes |
| Mesh Reduction | 0.3 | 0 | 0.95 |

TABLE 2

| Process Parameters for Forming Surface Roughness Lattice Surface Roughness Lattice | | | |
|---|---|---|---|
| Stochastic Lattice | Nominal | Min | Max |
| Rule | Surface Beam | NA | NA |
| Target Cell diameter (mm) | 0.008 | 0.0001 | 5 |

TABLE 2-continued

| Process Parameters for Forming Surface Roughness Lattice Surface Roughness Lattice | | | |
|---|---|---|---|
| Stochastic Lattice | Nominal | Min | Max |
| Random Seed | 1 | 0.01 | 1 |
| Minimum angle (°) | 0 | 0 | 359 |
| Maximum angle (°) | 90 | 359 | 0 |
| Length (mm) | 0.2 | 0.05 | 5 |
| Offset (mm) | 0 | 0 | 2.5 |
| Interactions | 35000 | 10000 | 10000000 |
| Mesh | | | |
| Mesh Resolution | 0 | 0 | 1 |
| Node Smoothing | 0 | 0 | 1 |
| Mesh Cleanup | Yes | No | Yes |
| Mesh Reduction | 0.5 | 0 | 0.95 |

The process parameters in the first column of Tables 1 and 2 will now be described. Initially, "Voronoi (Volume)" in Table 1 indicates that use of Voronoi Lattice has been selected which utilizes random seeds to break planar areas based on proximity to the seed. "Surface Beam" in Table 2 indicates that beams will be created from random seeds that are not connected at either end.

The first parameter is labeled "Target Cell diameter" and governs the desired average size of the Voronoi planar areas. The second parameter, labeled "Random Seed", is a number which is plugged into a random number generator of the 3D printing software to generate random seed locations. The third parameters in Table 1 and Table 2 are different. In Table 1, the third parameter is called "Diameter" and is related to a function of the 3D printing software where a zero thickness beam is first generated based on the process parameters, and the "Diameter" is the circular thickness input for the beams that have been generated. In Table 2, the third parameter is called "Minimum angle (°)" and represents the minimum angle of the beam from parallel to the surface thereof. Table 2 then includes four additional parameters which are not included in Table 1. First, "Maximum angle (°)" represents the maximum angle of the beam from parallel to the surface thereof. Next, Table 2 lists a "Length" parameter which represents the length of the beam which is generated. Table 2 then provides an "Offset" parameter which refers to the distance at which the generated beam is located from the surface. Finally, Table 2 provides an "Interactions" parameter which defines the density of the random seeds. The higher the number of interactions, the more random seeds are generated.

Next, the first column of both Tables 1 and 2 provides process parameters for a function called "Mesh", which generates an exportable mesh used to print the lattice. The "Mesh Resolution" parameter approximates the part to be printed and represents the number of polygons into which the approximated part is split so the mesh can be exported. The "Node Smoothing" parameter allows for control of the mesh resolution at the confluence of the lattice and solid members (i.e., the frame structure 120, 220, 320, 420, 520). As the number for Node Resolution moves from 0 to 1, the number of polygons used at the confluence of beams increases and effectively smooths the exported corners of a mesh. A finer mesh resolution results in the creation of smaller and more numerous polygons. The "Mesh Cleanup" parameter removes any beams which are not connected at both ends. Finally, the "Mesh Reduction" parameter reduces the triangle count of a mesh by a given percent.

In some non-limiting embodiments, the process parameters provided in Tables 1 and 2 create a porous structure 160, 260, 360, 460, 560 having volumetric density which ranges from about 0.1 $g/cm^3$ to about 5 $g/cm^3$ (and all values and ranges therebetween).

In accordance with other non-limiting embodiments, the process parameters provided in Tables 1 and 2 create a porous structure 160, 260, 360, 460, 560 formed of a series of overlapping layers in 3D space, resulting in a randomized pattern of voids and webs wherein: (a) the overlapping layers have an overlap of from about 5-100% (and all values and ranges therebetween); (b) the voids in the porous material have a size of from about 0.001-0.5 in. (and all values and ranges therebetween); and/or (c) webs in the porous material have a thickness of from about 0.0005-0.1 in. (and all values and ranges therebetween).

According to some other non-limiting embodiments, the process parameters provided in Table 2 create a porous structure 160, 260, 360, 460, 560 having an Ra surface roughness which is the same or different from the Ra surface roughness of the frame structure 120, 220, 320, 420, 520. Thus, the outer surfaces of porous structure 160, 260, 360, 460, 560 can have a roughness Ra of from about 0.1-1 micron (and all values and ranges therebetween).

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

What is claimed is:

1. An interbody implant device for use between bony structures and/or cartilage; said interbody implant includes a frame structure and a porous structure positioned at least partially within said frame structure; said interbody implant device includes a top surface, a bottom surface, a front wall, a rear wall, a first side wall, and a second side wall; said frame structure includes a rear plate, a front plate section, an outer top rim, an outer bottom rim, an inner top rim, and an inner bottom rim; said rear plate forms at least a portion of said rear wall; said front plate section forms at least a portion of said front wall; said outer top rim forms an outer peripheral edge of a portion of said interbody implant device; said outer bottom rim forms an outer peripheral edge of at least a portion of said interbody implant device; said outer top and bottom rims are spaced from one another; said rear plate is connected to at least one of said outer top rim, said outer bottom rim and combinations thereof; said front plate section is connected to at least one of said outer top rim, said outer bottom rim and combinations thereof; said inner top rim and said inner bottom rim are spaced from one another; said outer top rim is spaced from said inner top rim; said outer bottom rim is spaced from said inner bottom rim; said inner bottom rim defines a portion of an inner wall of a central opening in said interbody implant device; said inner top rim defines a portion of said inner wall of said central opening in said interbody implant device; said inner top rim and said inner bottom rim are spaced from at least one of said front wall, said rear wall and combinations thereof; said porous structure is absent support struts within an interior of said porous structure; said porous structure has volumetric density of 0.1 $g/cm^3$ to 5 $g/cm^3$; said porous structure forms a series of overlapping layers in 3D space resulting in a completely randomized pattern of voids and webs wherein (a) said overlapping layers have an overlap of 5-100%; (b) said voids in said porous material have a size of from about 0.001-0.5 in.; and (c) said webs in said porous material have a thickness of 0.0005-0.1 in.

2. The interbody implant device as defined in claim 1, wherein a bottom surface of said inner top rim is partially or fully absent said porous structure to form an upper undercut in said central opening; a top surface of said inner bottom rim is partially or fully absent said porous structure to form a lower undercut in said central opening.

3. The interbody implant device as defined in claim 2, wherein said outer top rim and said outer bottom rim are only connected together by said rear plate and said porous structure.

4. The interbody implant device as defined in claim 3, wherein said frame structure is absent struts connected to said outer top rim and said outer bottom rim.

5. The interbody implant device as defined in claim 4, wherein at least one of said top surface, said bottom surface rim, and combinations thereof includes one or more surface serrations or teeth.

6. The interbody implant device as defined in claim 5, wherein said front plate section includes top and bottom front plates; said top front plate is connected to said outer top rim; said bottom front plate is connected to said outer bottom rim; said rear plate is spaced from said top and bottom front plates.

7. The interbody implant device as defined in claim 6, wherein said top and bottom front plates are spaced from one another.

8. The interbody implant device as defined in claim 1, wherein said outer top rim and said outer bottom rim are only connected together by said rear plate and said porous structure.

9. The interbody implant device as defined in claim 1, wherein said frame structure is absent struts connected to said outer top rim and said outer bottom rim.

10. The interbody implant device as defined in claim 1, wherein at least one of said top surface, said bottom surface rim, and combinations thereof includes one or more surface serrations or teeth.

11. The interbody implant device as defined in claim 1, wherein said front plate section includes top and bottom front plates; said top front plate is connected to said outer top rim; said bottom front plate is connected to said outer bottom rim; said rear plate is spaced from said top and bottom front plates.

12. The interbody implant device as defined in claim 11, wherein said top and bottom front plates are spaced from one another.

* * * * *